United States Patent [19]

Kanda et al.

[11] Patent Number: 4,658,276
[45] Date of Patent: Apr. 14, 1987

[54] PHTHALIDE DERIVATIVES AND RECORDING SYSTEM UTILIZING THE SAME

[75] Inventors: Nobuo Kanda, Osaka; Tetsuro Horiike, Kanagawa; Mitsuru Kondo, Kawabe, all of Japan

[73] Assignee: Kanzaki Paper Manufacturing Co., Ltd., Tokyo, Japan

[21] Appl. No.: 872,865

[22] Filed: Jun. 11, 1986

[30] Foreign Application Priority Data

| Jun. 22, 1985 | [JP] | Japan | 60-136553 |
| Aug. 9, 1985 | [JP] | Japan | 60-176318 |
| Aug. 27, 1985 | [JP] | Japan | 60-189218 |
| Aug. 29, 1985 | [JP] | Japan | 60-190439 |
| Oct. 31, 1985 | [JP] | Japan | 60-245734 |

[51] Int. Cl.$^4$ .............. B41M 5/16; B41M 5/18; B41M 5/22
[52] U.S. Cl. .................. 346/220; 346/223; 427/151
[58] Field of Search .............. 346/217, 220, 223, 225; 427/151; 549/307, 308, 309

[56] References Cited

U.S. PATENT DOCUMENTS 4,591,888  5/1986  Satake et al. .................. 346/220

FOREIGN PATENT DOCUMENTS 124377  7/1984  European Pat. Off. ........... 346/221
2004294  3/1979  United Kingdom ............... 549/309

*Primary Examiner*—Bruce H. Hess
*Attorney, Agent, or Firm*—Fisher, Christen & Sabol

[57] ABSTRACT

A new phthalide derivative useful as a colorless chromogenic material has the following formula:

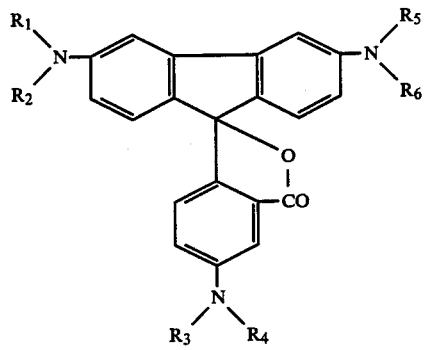

wherein $R_1$, $R_2$, $R_3$, $R_4$, $R_5$ and $R_6$ have the same meaning as defined hereinbefore.

3 Claims, No Drawings

PHTHALIDE DERIVATIVES AND RECORDING SYSTEM UTILIZING THE SAME

BACKGROUND OF THE INVENTION

This invention relates to phthalide derivatives as new compounds useful as colorless chromogenic materials, and a new recording system utilizing the same.

There are known various kinds of recording systems utilizing the colorforming reaction between a colorless chromogenic material and an electron accepting acidic reactant material by the medium of mechanical, heat, electric or light energy. Among them there are included a pressure sensitive record sheet, a heat sensitive record sheet, an electrothermal record sheet, an ultrasonic record sheet, an electron beam record sheet, an electrostatic record sheet and a photosensitive record sheet. The colorless chromogenic materials of these kinds also find their usefulness in typewriter ribbons, ball-point pen ink, crayon and stamp ink.

One of the most typical colorless chromogenic materials is crystal violet lactone. This dye material reacts with an electron accepting acidic treatment material upon contact to develop a clear color of bluish violet but the developed color has a poor light resistance so that the recorded images (color images) soon disappear in a short time when subjected to radiation of ultraviolet rays of day light. Another disadvantage of this type of dye is in the fact that the recorded images obtained with this material show no absorption for the infrared range of 700–900 nm and accordingly this type of dye material cannot be used for a reading machine utilizing an optical reading system responsive to infrared absorption.

Recently, there are disclosed certain kinds of phthalide derivatives having a similar structure to that of the phthalide derivatives according to this invention as substantially colorless chromogenic materials which are adapted for optical reading with near infrared rays in EP Application No. 84302885.3 (EP Publication No. 124377).

However, the record materials such as heat-sensitive record materials in which any of those phthalide derivatives is used are easily affected by temperature and humidity so that the produced color image is discolored. Resultantly, the difference between the light absorptions of the produced color image and the background at near infrared wavelength become to small to adapt them for optical reading.

The primary object of the invention is to provide novel phthalide derivatives superior in both of heat resistance and moisture resistance and useful as colorless chromogenic materials for use in various recording systems.

Another object of the invention is to provide novel colorless chromogenic material for use in recording systems in which the color images when developed therefrom have a good light resistance, especially, a good ultraviolet ray resistance.

A further object of the invention is to provide novel colorless chromogenic materials for use in recording systems in which the color images when developed therefrom show a good absorption for infrared rays.

It is also included among the objects of the invention to provide an improved recording system in which a phthalide derivative as a new compound is used as a colorless chromogenic material and the color images when developed therefrom are superior in each of heat resistance, moisture resistance and light resistance and show a good absorption for infrared rays.

Other objects and advantages of the invention will become apparent from the following description.

SUMMARY OF THE INVENTION

The novel phthalide derivatives according to the invention has the following formula:

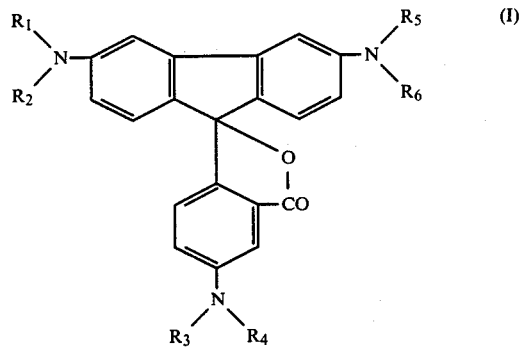

wherein at least one of $R_1$, $R_2$, $R_3$, $R_4$, $R_5$ and $R_6$ radicals is an alkoxyalkyl having 3 to 8 carbon atoms; an unsaturated alkyl having 3 to 9 carbon atoms; tetrahydrofurfuryl; tetrahydropyran-2-methyl; an aralkyl represented by the following formula

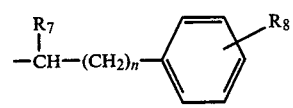

in which n is 0, 1 or 2, $R_7$ is hydrogen or an alkyl having 1 to 4 carbon atoms and $R_8$ is hydrogen, halogen, an alkyl having 1 to 4 carbon atoms or an alkoxyl having 1 to 4 carbon atoms, and when n is 0 and $R_7$ is hydrogen, $R_8$ is halogen or an alkoxyl having 1 to 4 carbon atoms; an alkyl having 2 to 8 carbon atoms and having phenoxy group which may be substituted by at least one selected from the group consisting of halogens, alkyls having 1 to 4 carbon atoms, and alkoxyls having 1 to 4 carbon atoms; or a halogenated alkyl having 1 to 8 carbon atoms; and each of the other ones ends of said radicals is hydrogen; an alkyl having 1 to 8 carbon atoms which may be substituted by at least one halogen; a cycloalkyl having 5 to 12 carbon atoms; an alkoxyalkyl having 3 to 8 carbon atoms; an unsaturated alkyl having 3 to 9 carbon atoms; tetrahydrofurfuryl; tetrahydropyran-2-methyl; an aralkyl which may be substituted by at least one selected from the group consisting of halogens, alkyls having 1 to 4 carbon atoms and alkoxyls having 1 to 4 carbon atoms; an aryl which may be substituted by at least one selected from the group consisting of halogens, alkyls having 1 to 4 carbon atoms and alkoxyls having 1 to 4 carbon atoms; or an alkyl having 2 to 8 carbon atoms and having phenoxy group which may be substituted by at least one selected from the group consisting of halogens, alkyls having 1 to 4 carbon atoms, and alkoxyls having 1 to 4 carbon atoms; or one or two pairs of $R_1$ and $R_2$, $R_3$ and $R_4$, and $R_5$ and $R_6$ may form morpholino, pyrrolidino, piperidino or hexamethyleneimino group together with the adjacent nitrogen atom.

The phthalide derivative having the above formula can be used as colorless chromogenic materials for use in various recording systems including a pressure sensitive recording system and a heat sensitive recording system. The compounds according to the invention can produce a clear and deep bluish color upon contact with an electron accepting acidic reactant material. The record materials comprising the phthalide derivatives according to the invention as chromogenic materials are stable under the circumstances of high humidity and high temperature. The produced color images have a good light resistance and can maintain the clear color tone initially produced for a long time. The color images also show a good absorption for infrared rays with the range of 700–900 nm so that they can be detected for reading in an infrared ray responsive optical reading machine.

DETAILED DESCRIPTION OF THE INVENTION

The phthalide derivatives represented by the formula (I) according to the invention may preferably be prepared by the following process:

In the first, 3-(p-aminophenyl)-6-aminophthalide derivatives represented by the formula (IV) may be prepared by heating p-aminobenzaldehyde derivatives represented by the formula (II) and m-aminobenzoic acid derivatives represented by the formula (III) in acetic acid anhydride to occur dehydration condensation between them.

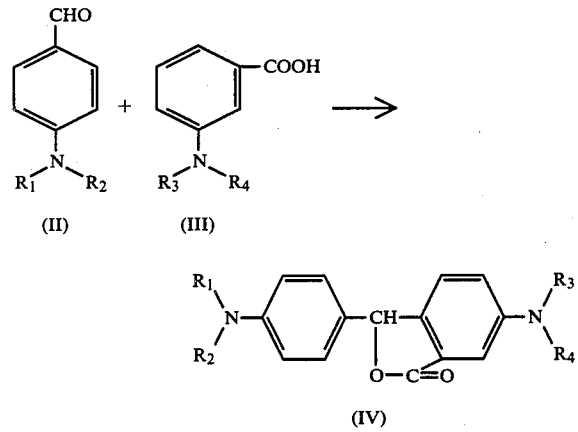

wherein $R_1$, $R_2$, $R_3$ and $R_4$ are the same as described above.

The 3-(p-aminophenyl)-6-aminophthalide derivatives represented by the formula (IV) are dissolved in an aqueous solution of sodium hydroxide and then oxidized with the use of sodium m-nitrobenzenesulfonate at 90°~100° C. to obtain 2-(p-aminobenzoyl)-5-aminobenzoic acid derivatives represented by the formula (V).

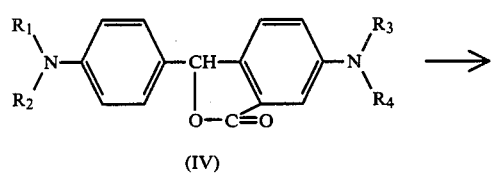

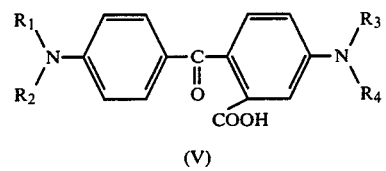

wherein $R_1$, $R_2$, $R_3$ and $R_4$ are the same as described above.

Then the benzoic acid derivatives represented by the formula (V) is made react with aniline derivatives (VI) with the use of dehydration condensation agents such as acetic anhydride and phosphorus oxychloride at a temperature of 50°~150° C. for a few hours to prepare triphenylmethane derivatives represented by the formula (VII).

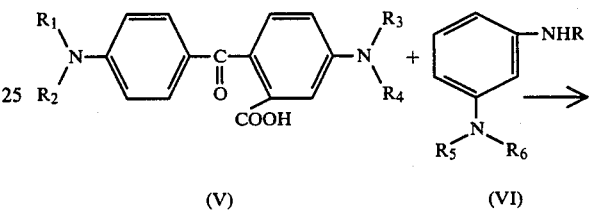

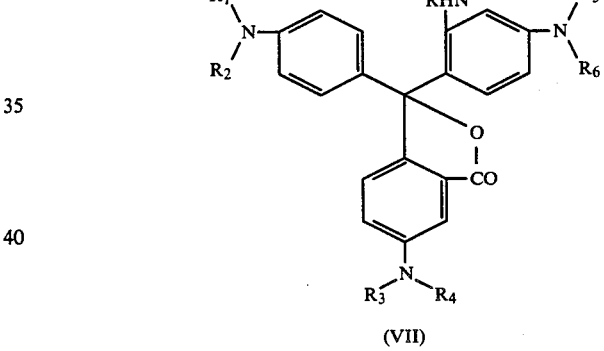

wherein R is hydrogen or acyl, and $R_1$, $R_2$, $R_3$, $R_4$, $R_5$ and $R_6$ are the same as described above.

When R of the triphenylmethane derivatives represented by the formula (VII) is acyl, triphenylmethane derivatives represented by the formula (VIII) may be prepared by the hydrolysis with alkali or acid.

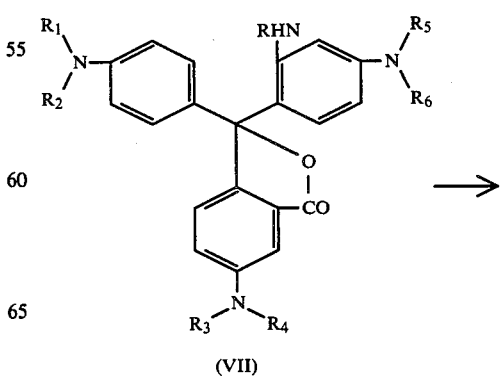

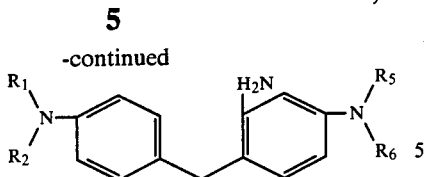

(VIII)

wherein R, $R_1$, $R_2$, $R_3$, $R_4$, $R_5$ and $R_6$ are the same as described above.

The phthalide derivatives represented by the formula (I) may be prepared by diazotizing the triphenylmethane derivatives represented by the formula (VIII) in sulfuric acid at a temperature of $-5°$ C. to $10°$ C. and then allowing to stand for a few hours to scores of hours in the presence of copper powder or copper compounds at a temperature of $0°$ C. to $100°$ C. to occur ring closure.

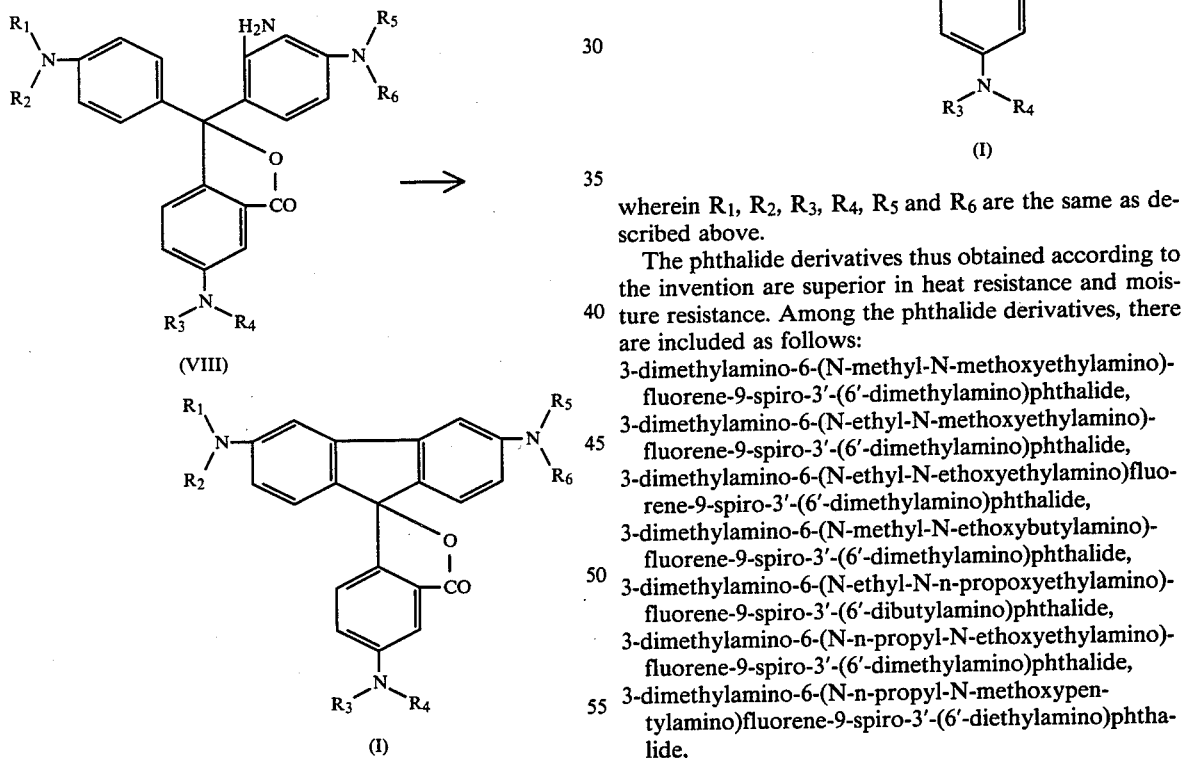

(VIII)

(I)

wherein $R_1$, $R_2$, $R_3$, $R_4$, $R_5$ and $R_6$ are the same as described above.

Alternatively, the phthalide derivatives represented by the formula (I) may be prepared by heating phthalide derivatives represented by the formula (IX) together with halogenated aluminum at $50°$ C. to $250°$ C., preferably $100°$ C. to $200°$ C., in the presence of at least one compound selected from the group consisting of amides such as urea, N-methylpyrrolidone, formamide, acetamide, dimethylformamide, propionamide, n-butylamide, n-valeramide, stearylamide, benzamide and the like;

acids such as formic acid, acetic acid, propionic acid, butyric acid, valeric acid, capric acid, caprylic acid, caproic acid, lauric acid, myristic acid, stearic acid, benzoic acid and the like; and salts thereof.

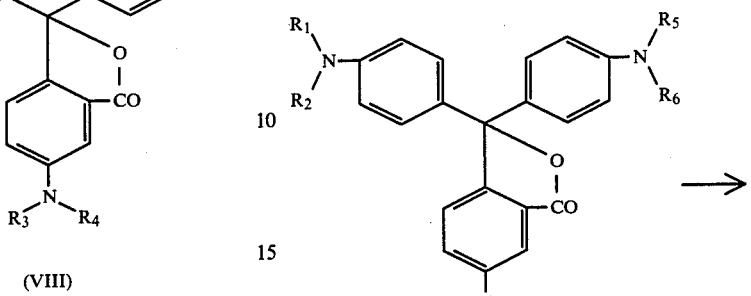

(IX)

(I)

wherein $R_1$, $R_2$, $R_3$, $R_4$, $R_5$ and $R_6$ are the same as described above.

The phthalide derivatives thus obtained according to the invention are superior in heat resistance and moisture resistance. Among the phthalide derivatives, there are included as follows:

3-dimethylamino-6-(N-methyl-N-methoxyethylamino)-fluorene-9-spiro-3'-(6'-dimethylamino)phthalide, 3-dimethylamino-6-(N-ethyl-N-methoxyethylamino)-fluorene-9-spiro-3'-(6'-dimethylamino)phthalide, 3-dimethylamino-6-(N-ethyl-N-ethoxyethylamino)fluorene-9-spiro-3'-(6'-dimethylamino)phthalide, 3-dimethylamino-6-(N-methyl-N-ethoxybutylamino)-fluorene-9-spiro-3'-(6'-dimethylamino)phthalide, 3-dimethylamino-6-(N-ethyl-N-n-propoxyethylamino)-fluorene-9-spiro-3'-(6'-dibutylamino)phthalide, 3-dimethylamino-6-(N-n-propyl-N-ethoxyethylamino)-fluorene-9-spiro-3'-(6'-dimethylamino)phthalide, 3-dimethylamino-6-(N-n-propyl-N-methoxypentylamino)fluorene-9-spiro-3'-(6'-diethylamino)phthalide, 3-dimethylamino-6-(N-ethyl-N-methoxyethylamino)-fluorene-9-spiro-3'-(6'-diethylamino)phthalide, 3-dimethylamino-6-(N-isopropyl-N-methoxyethylamino)fluorene-9-spiro-3'-(6'-dimethylamino)phthalide, 3-dimethylamino-6-(N-isopropyl-N-n-hexyloxyethylamino)fluorene-9-spiro-3'-(6'-dimethylamino)phthalide, 3-dimethylamino-6-(N-isopropyl-N-ethoxypropylamino)fluorene-9-spiro-3'-(6'-dioctylamino)phthalide, 3-dimethylamino-6-(N-n-butyl-N-ethoxyhexylamino)-fluorene-9-spiro-3'-(6'-diethylamino)phthalide,
3-dimethylamino-6-(N-n-butyl-N-methoxyethylamino)-fluorene-9-spiro-3'-(6'-diethylamino)phthalide,
3-dimethylamino-6-(N-n-amyl-N-n-propoxyethylamino)fluorene-9-spiro-3'-(6'-dimethylamino)phthalide,
3-dimethylamino-6-(N-isoamyl-N-methoxyethylamino)fluorene-9-spiro-3'-(6'-dimethylamino)phthalide,
3-dimethylamino-6-(N-n-amyl-N-ethoxyethylamino)-fluorene-9-spiro-3'-(6'-dimethylamino)phthalide,
3-dimethylamino-6-(N-isoamyl-N-ethoxybutylamino)-fluoroene-9-spiro-3'-(6'-dimethylamino)phthalide,
3-dimethylamino-6-(N-n-octyl-N-ethoxybutylamino)-fluorene-9-spiro-3'-(6'-diethylamino)phthalide,
3-dimethylamino-6-(N-n-octyl-N-methoxyethylamino)-fluorene-9-spiro-3'-(6'-dibutylamino)phthalide,
3-dimethylamino-6-(N-n-heptyl-N-n-propoxyethylamino)fluorene-9-spiro-3'-(6'-dimethylamino)phthalide,
3-dimethylamino-6-(N-n-heptyl-N-ethoxyethylamino)-fluorene-9-spiro-3'-(6'-dimethylamino)phthalide,
3-dimethylamino-6-dimethoxyethylaminofluorene-9-spiro-3'-(6'-diethylamino)phthalide,
3-dimethylamino-6-diethoxyethylaminofluorene-9-spiro-3'-(6'-dipropylamino)phthalide,
3-diethylamino-6-(N-methyl-N-methoxyethylamino)-fluorene-9-spiro-3'-(6'-dimethylamino)phthalide,
3-diethylamino-6-(N-ethyl-N-ethoxyethylamino)fluorene-9-spiro-3'-(6'-dimethylamino)phthalide,
3-diethylamino-6-(N-methyl-N-methoxyethylamino)-fluorene-9-spiro-3'-(6'-dioctylamino)phthalide,
3-diethylamino-6-(N-ethyl-N-methoxypentylamino)-fluorene-9-spiro-3'-(6'-dimethylamino)phthalide,
3-diethylamino-6-(N-tert-butyl-N-ethoxyethylamino)-fluorene-9-spiro-3'-(6'-diethylamino)phthalide,
3-diethylamino-6-(N-n-amyl-N-n-butoxyethylamino)-fluorene-9-spiro-3'-(6'-dimethylamino)phthalide,
3-di-n-butylamino-6-(N-methyl-N-methoxyethylamino)fluorene-9-spiro-3'-(6'-dimethylamino)phthalide,
3-di-n-butylamino-6-(N-methyl-N-ethoxyethylamino)-fluorene-9-spiro-3'-(6'-dimethylamino)phthalide,
3-di-n-butylamino-6-(N-isopropyl-N-ethoxypropylamino)fluorene-9-spiro-3'-(6'-diethylamino)phthalide,
3-di-n-butylamino-6-(N-n-octyl-N-methoxyethylamino)fluorene-9-spiro-3'-(6'-dimethylamino)phthalide,
3-di-n-butylamino-6-(N-hepty-N-methoxyheptylamino)fluorene-9-spiro-3'-(6'-dimethylamino)phthalide,
3-di-n-hexylamino-6-(N-ethyl-N-methoxyethylamino)-fluorene-9-spiro-3'-(6'-dimethylamino)phthalide,
3-di-n-hexylamino-6-(N-tert-butyl-N-ethoxyethylamino)fluorene-9-spiro-3'-(6'-diethylamino)phthalide,
3-di-n-hexylamino-6-(N-methyl-N-methoxybutylamino)fluorene-9-spiro-3'-(6'-diethylamino)phthalide,
3-di-n-hexylamino-6-dimethoxyethylaminofluorene-9-spiro-3'-(6'-diethylamino)phthalide,
3-di-n-octylamino-6-(N-methyl-N-methoxypropylamino)fluorene-9-spiro-3'-(6'-dimethylamino)phthalide,
3-(N-methyl-N-ethylamino)-6-(N-ethyl-N-n-propoxyethylamino)fluorene-9-spiro-3'-(6'-dimethylamino)phthalide,
3-(N-ethyl-N-n-butylamino)-6-(N-methyl-N-n-pentyloxyethylamino)fluorene-9-spiro-3'-(6'-dimethylamino)phthalide,
3-(N-ethyl-N-n-hexylamino)-6-(N-n-butyl-N-methoxyethylamino)fluorene-9-spiro-3'-(6'-dipentylamino)phthalide,
3-ethylamino-6-(N-ethyl-N-ethoxypentylamino)fluorene-9-spiro-3'-(6'-dimethylamino)phthalide,
3-n-butylamino-6-dimethoxyethylaminofluorene-9-spiro-3'-(6'-dimethylamino)phthalide,
3-(N-tert-butyl-N-n-octylamino)-6-diethoxyethylaminofluorene-9-spiro-3'-(6'-dimethylamino)phthalide,
3-amino-6-dimethoxyethylaminofluorene-9-spiro-3'-(6'-dimethylamino)phthalide,
3-amino-6-(N-methyl-N-ethoxyethylamino)fluorene-9-spiro-3'-(6'-diethylamino)phthalide,
3-(N-n-hexyl-N-n-octylamino)-6-(N-ethyl-N-methoxyethylamino)fluorene-9-spiro-3'-(6'-dimethylamino)phthalide,
3-(N-isoamyl-N-ethylamino)-6-(N-ethyl-N-ethoxyethylamino)fluorene-9-spiro-3'-(6'-diethylamino)phthalide,
3-morpholino-6-(N-methyl-N-methoxyethylamino)-fluorene-9-spiro-3'-(6'-diethylamino)phthalide,
3-morpholino-6-diethoxyethylaminofluorene-9-spiro-3'-(6'-dimethylamino)phthalide,
3-pyrrolidino-6-(N-ethyl-N-ethoxyethylamino)fluorene-9-spiro-3'-(6'-dimethylamino)phthalide,
3-pyrrolidino-6-(N-ethyl-N-ethoxyethylamino)fluorene-9-spiro-3'-(6'-pyrrolidino)phthalide,
3-pyrrolidino-6-(N-n-butyl-N-n-pentyloxyethylamino)-fluorene-9-spiro-3'-(6'-dibutylamino)phthalide,
3-pyrrolidino-6-dimethoxyethylaminofluorene-9-spiro-3'-(6'-diethylamino)phthalide,
3-piperidino-6-(N-methyl-N-methoxyethylamino)fluorene-9-spiro-3'-(6'-dipropylamino)phthalide,
3-piperidino-6-(N-isopropyl-N-ethoxyethylamino)fluorene-9-spiro-3'-(6'-diethylamino)phthalide,
3-piperidino-6-(N-n-octyl-N-ethoxyethylamino)fluorene-9-spiro-3'-(6'-dibutylamino)phthalide,
3-hexamethyleneimino-6-(N-ethyl-N-methoxyethylamino)fluorene-9-spiro-3'-(6'-dioctylamino)phthalide,
3-β-pipecolino-6-(N-ethyl-N-methoxyethylamino)fluorene-9-spiro-3'-(6'-dimethylamino)phthalide,
3-(N-methyl-N-cyclohexylamino)-6-(N-ethyl-N-ethoxyethylamino)fluorene-9-spiro-3'-(6'-dimethylamino)phthalide,
3-(N-cyclohexyl-N-methylamino)-6-(N-methyl-N-methoxybutylamino)fluorene-9-spiro-3'-(6'-diethylamino)phthalide,
3-(N-cyclopentyl-N-ethylamino)-6-(N-ethyl-N-butoxyethylamino)fluorene-9-spiro-3'-(6'-dibutylamino)phthalide,
3-(N-3,3,5-trimethylcyclohexyl-N-ethylamino)-6-(N-ethyl-N-n-butoxybutylamino)fluorene-9-spiro-3'-(6'-dimethylamino)phthalide,
3-(N-cyclododecyl-N-n-butylamino)-6-(N-methyl-N-ethoxypentylamino)fluorene-9-spiro-3'-(diethylamino)phthalide,
3-(N-phenyl-N-methylamino)-6-(N-methyl-N-n-pentyloxyethylamino)fluorene-9-spiro-3'-(6'-diethylamino)phthalide, 3-(N-p-tolyl-N-methylamino)-6-(N-methyl-N-methoxyethylamino)fluorene-9-spiro-3'-(6'-diethylamino)phthalide,
3-(N-xylidyl-N-ethylamino)-6-(N-ethyl-N-methoxypropylamino)fluorene-9-spiro-3'-(6'-diethylamino)phthalide,
3-(N-ethyl-p-chloroanilino)-6-(N-methyl-N-methoxyhexylamino)fluorene-9-spiro-3'-(6'-dibutylamino)phthalide,
3-(N-ethyl-p-tert-butylanilino)-6-(N-n-butyl-N-n-propoxyethylamino)fluorene-9-spiro-3'-(6'-dimethylamino)phthalide,
3-(N-methyl-p-ethoxyanilino)-6-(N-methyl-N-ethoxyethylamino)fluorene-9-spiro-3'-(6'-dimethylamino)phthalide,
3-(N-methyl-N-benzylamino)-6-(N-isoamyl-N-ethoxyethylamino)fluorene-9-spiro-3'-(6'-dibutylamino)phthalide,
3-(N-methyl-N-chlorobenzylamino)-6-(N-n-propyl-N-ethoxyhexylamino)fluorene-9-spiro-3'-(6'-dimethylamino)phthalide,
3-(N-n-propyl-N-m-ethylbenzylamino)-6-(N-n-amyl-N-ethoxyethylamino)fluorene-9-spiro-3'-(6'-diethylamino)phthalide,
3-(N-methyl-N-p-methoxybenzylamino)-6-(N-methyl-N-ethoxyethylamino)fluorene-9-spiro-3'-(6'-dimethylamino)phthalide,
3-(N-n-butyl-cyclohexylmethylamino)-6-(N-n-butyl-N-methoxyethylamino)fluorene-9-spiro-3'-(6'-diethylamino)phthalide,
3-(N-isopropyl-N-phenylethylamino)-6-(N-methyl-N-ethoxyhexylamino)fluorene-9-spiro-3'-(6'-dipropylamino)phthalide,
3,6-bis(N-ethyl-N-ethoxyethylamino)fluorene-9-spiro-3'-(6'-dimethylamino)phthalide,
3,6-bis(dimethoxybutylamino)fluorene-9-spiro-3'-(6'-dihexylamino)phthalide,
3,6-bis(N-phenyl-N-n-hexyloxyethylamino)fluorene-9-spiro-3'-(6'-dimethylamino)phthalide,
3,6-bis(N-cyclohexyl-N-n-propoxybutylamino)fluorene-9-spiro-3'-(6'-diethylamino)phthalide,
3-(N,N-dibutoxybutylamino)-6-(N-ethyl-N-ethoxyethylamino)fluorene-9-spiro-3'-(6'-diethylamino)phthalide,
3-(N-methoxyethyl-N-p-tolylamino)-6-(N-methyl-N-ethoxyethylamino)fluorene-9-spiro-3'-(6'-dimethylamino)phthalide,
3-(N-methoxypropyl-N-ethylamino)-6-(N-ethyl-N-n-butoxyethylamino)fluorene-9-spiro-3'-(6'-dimethylamino)phthalide,
3-(N-ethoxybutyl-N-n-butylamino)-6-(N-methyl-N-ethoxypropylamino)fluorene-9-spiro-3'-(6'-dimethylamino)phthalide,
3-(N-butoxyethyl-N-methylamino)-6-(N-propyl-N-ethoxybutylamino)fluorene-9-spiro-3'-(6'-diethylamino)phthalide,
3-pyrrolidino-6-(N-n-butyl-N-isopropoxyethylamino)fluorene-9-spiro-3'-(6'-pyrrolidino)phthalide,
3-(N-ethyl-N-methylamino)-6-(N-ethyl-N-ethoxyethylamino)fluorene-9-spiro-3'-(6'-pyrrolidino)phthalide,
3-(N-ethyl-N-p-tolylamino)-6-(N-methyl-N-methoxybutylamino)fluorene-9-spiro-3'-(6'-piperidino)phthalide,
3-(N-methyl-N-ethoxyethylamino)-6-(N-ethyl-N-tert-butoxyethylamino)fluorene-9-spiro-3'-(6'-N-ethyl-N-p-chloranilino)phthalide,
3,6-bis(N-ethyl-N-ethoxyethylamino)fluorene-9-spiro-3'-(6'-N-ethyl-N-ethoxyethylamino)phthalide,
3-dimethylamino-6-(N-methyl-N-n-propoxybutylamino)fluorene-9-spiro-3'-(6'-N-n-butylamino)phthalide,
3-diethylamino-6-(N-n-pentyloxyethylamino)fluorene-9-spiro-3'-(6'-dimethylamino)phthalide,
3-dimethylamino-6-(N-ethyl-N-ethoxyethylamino)fluorene-9-spiro-3'-(6'-N-methyl-N-ethylamino)phthalide;
3-dimethylamino-6-(N-methyl-N-allylamino)fluorene-9-spiro-3'-(6'-dimethylamino)phthalide,
3-dimethylamino-6-(N-methyl-N-propargylamino)fluorene-9-spiro-3'-(6'-dimethylamino)phthalide,
3-dimethylamino-6-(N-ethyl-N-allylamino)fluorene-9-spiro-3'-(6'-dibutylamino)phthalide,
3-dimethylamino-6-(N-n-propyl-N-allylamino)fluorene-9-spiro-3'-(6'-dimethylamino)phthalide,
3-dimethylamino-6-(N-n-propyl-N-allylamino)fluorene-9-spiro-3'-(6'-diethylamino)phthalide,
3-dimethylamino-6-(N-ethyl-N-allylamino)fluorene-9-spiro-3'-(6'-diethylamino)phthalide,
3-dimethylamino-6-(N-isopropyl-N-allylamino)fluorene-9-spiro-3'-(6'-dimethylamino)phthalide,
3-dimethylamino-6-(N-isopropyl-N-allylamino)fluorene-9-spiro-3'-(6'-diethylamino)phthalide,
3-dimethylamino-6-(N-isopropyl-N-allylamino)fluorene-9-spiro-3'-(6'-dioctylamino)phthalide,
3-dimethylamino-6-(N-n-butyl-N-allylamino)fluorene-9-spiro-3'-(6'-dimethylamino)phthalide,
3-dimethylamino-6-(N-n-butyl-N-allylamino)fluorene-9-spiro-3'-(6'-diethylamino)phthalide,
3-dimethylamino-6-(N-n-amyl-N-allylamino)fluorene-9-spiro-3'-(6'-dimethylamino)phthalide,
3-dimethylamino-6-(N-isoamyl-N-allylamino)fluorene-9-spiro-3'-(6'-dimethylamino)phthalide,
3-dimethylamino-6-(N-n-hexyl-N-allylamino)fluorene-9-spiro-3'-(6'-dimethylamino)phthalide,
3-dimethylamino-6-(N-n-octyl-N-allylamino)fluorene-9-spiro-3'-(6'-dimethylamino)phthalide,
3-dimethylamino-6-(N-methyl-N-2-butenylamino)fluorene-9-spiro-3'-(6'-dimethylamino)phthalide,
3-dimethylamino-6-(N-n-octyl-N-2-butenylamino)fluorene-9-spiro-3'-(6'-dimethylamino)phthalide,
3-dimethylamino-6-(N-methyl-N-2-methylallylamino)fluorene-9-spiro-3'-(6'-dibutylamino)phthalide,
3-dimethylamino-6-(N-methyl-N-2-ethylallylamino)fluorene-9-spiro-3'-(6'-dimethylamino)phthalide,
3-dimethylamino-6-(N-methyl-N-cinnamylamino)fluorene-9-spiro-3'-(6'-dimethylamino)phthalide,
3-dimethylamino-6-(diallylamino)fluorene-9-spiro-3'-(6'-dimethylamino)phthalide,
3-dimethylamino-6-diallylaminofluorene-9-spiro-3'-(6'-diethylamino)phthalide,
3-dimethylamino-6-diallylaminofluorene-9-spiro-3'-(6'-dipropylamino)phthalide,
3-diethylamino-6-(N-methyl-N-allylamino)fluorene-9-spiro-3'-(6'-dimethylamino)phthalide,
3-diethylamino-6-(N-ethyl-N-allylamino)fluorene-9-spiro-3'-(6'-dimethylamino)phthalide,
3-diethylamino-6-(N-tert-butyl-N-allylamino)fluorene-9-spiro-3'-(6'-diethylamino)phthalide,
3-diethylamino-6-(N-n-amyl-N-allylamino)fluorene-9-spiro-3'-(6'-dimethylamino)phthalide,
3-di-n-butylamino-6-(N-methyl-N-allylamino)fluorene-9-spiro-3'-(6'-dimethylamino)phthalide,
3-di-n-butylamino-6-(N-ethyl-N-allylamino)fluorene-9-spiro-3'-(6'-dimethylamino)phthalide, 3-di-n-butylamino-6-(N-isopropyl-N-allylamino)fluorene-9-spiro-3'-(6'-diethylamino)phthalide,
3-di-n-butylamino-6-(N-n-octyl-N-allylamino)fluorene-9-spiro-3'-(6'-dimethylamino)phthalide,
3-di-n-butylamino-6-(N-heptyl-N-allylamino)fluorene-9-spiro-3'-(6'-dimethylamino)phthalide,
3-di-n-hexylamino-6-(N-ethyl-N-allylamino)fluorene-9-spiro-3'-(6'-dimethylamino)phthalide,
3-dimethylamino-6-(N-methyl-N-2-butenylamino)fluorene-9-spiro-3'-(6'-dimethylamino)phthalide,
3-dimethylamino-6-(N-methyl-N-2-pentenylamino)fluorene-9-spiro-3'-(6'-dimethylamino)phthalide,
3-dimethylamino-6-(N-methyl-N-3-phenyl-2-propenylamino)fluorene-9-spiro-3'-(6'-dimethylamino)phthalide,
3-(N-methyl-N-ethylamino)-6-(N-ethyl-N-allylamino)fluorene-9-spiro-3'-(6'-dimethylamino)phthalide,
3-(N-ethyl-N-n-butylamino)-6-(N-methyl-N-allylamino)fluorene-9-spiro-3'-(6'-dimethylamino)phthalide,
3-(N-ethyl-N-n-hexylamino)-6-(N-n-butyl-N-allylamino)fluorene-9-spiro-3'-(6'-dimethylamino)phthalide,
3-dimethylamino-6-(N-allyl-N-ethoxyethylamino)fluorene-9-spiro-3'-(6'-dimethylamino)phthalide,
3-diallylamino-6-dimethoxyethylaminofluorene-9-spiro-3'-(6'-dimethylamino)phthalide,
3-(N-methyl-N-n-ethoxypropylamino)-6-diallylaminofluorene-9-spiro-3'-(6'-dimethylamino)phthalide,
3,6-bis(N-methyl-N-allylamino)fluorene-9-spiro-3'-(6'-dimethylamino)phthalide,
3,6-bis(N-ethyl-N-allylamino)fluorene-9-spiro-3'-(6'-diethylamino)phthalide,
3-morpholino-6-(N-methyl-N-allylamino)fluorene-9-spiro-3'-(6'-diethylamino)phthalide,
3-morpholino-6-diallylaminofluorene-9-spiro-3'-(6'-dimethylamino)phthalide,
3-pyrrolidino-6-(N-ethyl-N-allylamino)fluorene-9-spiro-3'-(6'-dimethylamino)phthalide,
3-pyrrolidino-6-(N-methyl-N-allylamino)fluorene-9-spiro-3'-(6'-dimethylamino)phthalide,
3-pyrrolidino-6-(N-ethyl-N-2-butenylamino)fluorene-9-spiro-3'-(6'-pyrrolidino)phthalide,
3-pyrrolidino-6-diallylaminofluorene-9-spiro-3'-(6'-diethylamino)phthalide,
3-piperidino-6-(N-methyl-N-allylamino)fluorene-9-spiro-3'-(6'-dipropylamino)phthalide,
3-piperidino-6-(N-isopropyl-N-allylamino)fluorene-9-spiro-3'-(6'-diethylamino)phthalide,
3-piperidino-6-(N-n-octyl-N-allylamino)fluorene-9-spiro-3'-(6'-dibutylamino)phthalide,
3-hexamethyleneimino-6-(N-ethyl-N-allylamino)fluorene-9-spiro-3'-(6'-dimethylamino)phthalide,
3-β-pipecolino-6-(N-ethyl-N-allylamino)fluorene-9-spiro-3'-(6'-dimethylamino)phthalide,
3-(N-cyclohexyl-N-methylamino)-6-(N-methyl-N-allylamino)fluorene-9-spiro-3'-(6'-diethylamino)phthalide,
3-(N-methyl-N-cyclohexylamino)-6-(N-ethyl-N-propargylamino)fluorene-9-spiro-3'-(6'-dimethylamino)phthalide,
3-(N-cyclopentyl-N-ethylamino)-6-(N-ethyl-N-allylamino)fluorene-9-spiro-3'-(6'-dimethylamino)phthalide,
3-(N-3',3',5'-trimethylcyclohexyl-N-ethylamino)-6-(N-ethyl-N-allylamino)fluorene-9-spiro-3'-(6'-dimethylamino)phthalide,
3-(N-cyclododecyl-N-n-butylamino)-6-(N-methyl-N-allylamino)fluorene-9-spiro-3'-(6'-diethylamino)phthalide,
3-(N-phenyl-N-methylamino)-6-(N-methyl-N-allylamino)fluorene-9-spiro-3'-(6'-diethylamino)phthalide,
3-(N-p-tolyl-N-methylamino)-6-(N-methyl-N-allylamino)fluorene-9-spiro-3'-(6'-diethylamino)phthalide,
3-(N-xylidyl-N-ethylamino)-6-(N-ethyl-N-2-methylallylamino)fluorene-9-spiro-3'-(6'-diethylamino)phthalide,
3-(N-ethyl-N-p-chloroanilino)-6-(N-methyl-N-2-ethylallylamino)fluorene-9-spiro-3'-(6'-dimethylamino)phthalide,
3-(N-ethyl-N-p-tert-butylanilino)-6-(N-n-methyl-N-2-butenylamino)fluorene-9-spiro-3'-(6'-dimethylamino)phthalide,
3-(N-methyl-N-p-ethoxyanilino)-6-(N-methyl-N-propargylamino)fluorene-9-spiro-3'-(6'-dimethylamino)phthalide,
3-(N-methyl-N-benzylamino)-6-(N-methyl-N-2-butenylamino)fluorene-9-spiro-3'-(6'-dimethylamino)phthalide,
3-(N-methyl-N-chlorobenzylamino)-6-(N-methyl-N-2-pentenylamino)fluorene-9-spiro-3'-(6'-dimethylamino)phthalide,
3-(N-methyl-N-p-methylbenzylamino)-6-(N-methyl-N-cinnamylamino)fluorene-9-spiro-3'-(6'-diethylamino)phthalide,
3-(N-methyl-N-p-methoxybenzylamino)-6-(N-methyl-N-3-phenyl-2-propenylamino)fluorene-9-spiro-3'-(6'-dimethylamino)phthalide,
3-(N-n-butyl-N-cyclohexylmethylamino)-6-(N-n-butyl-N-propargylamino)fluorene-9-spiro-3'-(6'-diethylamino)phthalide,
3-(N-isopropyl-N-phenylethylamino)-6-(N-methyl-N-propargylamino)fluorene-9-spiro-3'-(6'-dipropylamino)phthalide,
3,6-bis(N-ethyl-N-propargylamino)fluorene-9-spiro-3'-(6'-dimethylamino)phthalide,
3,6-bis(N-allyl-N-n-ethoxybutylamino)fluorene-9-spiro-3'-(6'-diethylamino)phthalide,
3-(N,N-diallylamino)-6-(N-ethyl-N-allylamino)fluorene-9-spiro-3'-(6'-diethylamino)phthalide,
3-(N-allyl-N-p-tolylamino)-6-(N-methyl-N-allylamino)fluorene-9-spiro-3'-(6'-dimethylamino)phthalide,
3-(N-propargyl-N-ethylamino)-6-(N-ethyl-N-allylamino)fluorene-9-spiro-3'-(6'-dimethylamino)phthalide,
3-pyrrolidino-6-(N-n-butyl-N-allylamino)fluorene-9-spiro-3'-(6'-pyrrolidino)phthalide,
3-(N-ethyl-N-methylamino)-6-(N-ethyl-N-allylamino)fluorene-9-spiro-3'-(6'-pyrrolidino)phthalide,
3-(N-ethyl-N-p-tolylamino)-6-(N-methyl-N-propargylamino)fluorene-9-spiro-3'-(6'-piperidino)phthalide,
3-(N-methyl-N-allylamino)-6-(N-ethyl-N-propargylamino)fluorene-9-spiro-3'-(6'-N-ethyl-p-chloroanilino)phthalide,
3,6-bis(N-ethyl-N-allylamino)fluorene-9-spiro-3'-(6'-N-methyl-N-ethoxyethylamino)phthalide,
3-dimethylamino-6-(N-ethyl-N-allylamino)fluorene-9-spiro-3'-(6'-N-methyl-N-ethylamino)phthalide;
3-dimethylamino-6-(N-methyl-N-tetrahydrofurfurylamino)fluorene-9-spiro-3'-(6'-dimethylamino)phthalide, 3-dimethylamino-6-(N-ethyl-N-tetrahydrofur-furylamino)fluorene-9-spiro-3'-(6'-dimethylamino)phthalide, 3-dimethylamino-6-(N-allyl-N-tetrahydrofur-furylamino)fluorene-9-spiro-3'-(6'-dimethylamino)phthalide, 3-dimethylamino-6-(N-methyl-N-tetrahydropyran-2-methylamino)fluorene-9-spiro-3'-(6'-dimethylamino)phthalide, 3-dimethylamino-6-(N-ethyl-N-tetrahydrofur-furylamino)fluorene-9-spiro-3'-(6'-dibutylamino)phthalide, 3-dimethylamino-6-(N-n-propyl-N-tetrahydrofur-furylamino)fluorene-9-spiro-3'-(6'-dimethylamino)phthalide, 3-dimethylamino-6-(N-n-propyl-N-tetrahydrofur-furylamino)fluorene-9-spiro-3'-(6'-diethylamino)phthalide, 3-dimethylamino-6-(N-ethyl-N-tetrahydrofuran-2-methylamino)fluorene-9-spiro-3'-(6'-diethylamino)phthalide, 3-dimethylamino-6-(N-isopropyl-N-tetrahydrofur-furylamino)fluorene-9-spiro-3'-(6'-dimethylamino)phthalide, 3-dimethylamino-6-(N-isopropyl-N-tetrahydropyran-2-methylamino)fluorene-9-spiro-3'-(6'-dimethylamino)phthalide, 3-dimethylamino-6-(N-isopropyl-N-tetrahydrofur-furylamino)fluorene-9-spiro-3'-(6'-dioctylamino)phthalide, 3-dimethylamino-6-(N-n-butyl-N-tetrahydrofur-furylamino)fluorene-9-spiro-3'-(6'-diethylamino)phthalide, 3-dimethylamino-6-(N-tetrahydrofurfuryl-N-methoxyethylamino)fluorene-9-spiro-3'-(6'-diethylamino)phthalide, 3-dimethylamino-6-(N-n-amyl-N-tetrahydrofur-furylamino)fluorene-9-spiro-3'-(6'-dimethylamino)phthalide, 3-dimethylamino-6-(N-isoamyl-N-tetrahydrofur-furylamino)fluorene-9-spiro-3'-(6'-dimethylamino)phthalide, 3-dimethylamino-6-(N-n-amyl-N-tetrahydropyran-2-methylamino)fluorene-9-spiro-3'-(6'-dimethylamino)phthalide, 3-dimethylamino-6-(N-tetrahydrofurfuryl-N-ethoxybutylamino)fluorene-9-spiro-3'-(6'-dimethylamino)phthalide, 3-dimethylamino-6-(N-n-octyl-N-tetrahydrofur-furylamino)fluorene-9-spiro-3'-(6'-diethylamino)phthalide, 3-dimethylamino-6-(N-n-octyl-N-tetrahydrofur-furylamino)fluorene-9-spiro-3'-(6'-dibutylamino)phthalide, 3-dimethylamino-6-(N-n-heptyl-N-tetrahydrofur-furylamino)fluorene-9-spiro-3'-(6'-dimethylamino)phthalide, 3-dimethylamino-6-(N-n-heptyl-N-tetrahydropyran-2-methylamino)fluorene-9-spiro-3'-(6'-dimethylamino)phthalide, 3-dimethylamino-6-ditetrahydrofurfurylaminofluorene-9-spiro-3'-(6'-diethylamino)phthalide, 3-dimethylamino-6-ditetrahydrofurfurylaminofluorene-9-spiro-3'-(6'-dipropylamino)phthalide, 3-diethylamino-6-(N-methyl-N-tetrahydrofur-furylamino)fluorene-9-spiro-3'-(6'-dimethylamino)phthalide, 3-diethylamino-6-(N-ethyl-N-tetrahydrofur-furylamino)fluorene-9-spiro-3'-(6'-dimethylamino)phthalide, 3-diethylamino-6-(N-2-butene-N-tetrahydropyran-2-methylamino)fluorene-9-spiro-3'-(6'-dioctylamino)phthalide, 3-diethylamino-6-(N-tetrahydrofurfuryl-N-methoxypentylamino)fluorene-9-spiro-3'-(6'-dimethylamino)phthalide, 3-diethylamino-6-(N-tert-butyl-N-tetrahydrofur-furylamino)fluorene-9-spiro-3'-(6'-diethylamino)phthalide, 3-diethylamino-6-(N-tetrahydrofurfuryl-N-n-butoxyethylamino)fluorene-9-spiro-3'-(6'-dimethylamino)phthalide, 3-di-n-butylamino-6-(N-methyl-N-tetrahydrofur-furylamino)fluorene-9-spiro-3'-(6'-dimethylamino)phthalide, 3-di-n-butylamino-6-(N-ethyl-N-tetrahydrofur-furylamino)fluorene-9-spiro-3'-(6'-dimethylamino)phthalide, 3-di-n-butylamino-6-(N-methyl-N-tetrahydropyran-2-methylamino)fluorene-9-spiro-3'-(6'-dimethylamino)phthalide, 3-di-n-butylamino-6-(N-isopropyl-N-tetrahydrofur-furylamino)fluorene-9-spiro-3'-(6'-diethylamino)phthalide, 3-di-n-butylamino-6-(N-n-octyl-N-tetrahydrofur-furylamino)fluorene-9-spiro-3'-(6'-dimethylamino)phthalide, 3-di-n-butylamino-6-(N-heptyl-N-tetrahydropyran-2-methylamino)fluorene-9-spiro-3'-(6'-dimethylamino)phthalide, 3-di-n-hexylamino-6-(N-ethyl-N-tetrahydrofur-furylamino)fluorene-9-spiro-3'-(6'-dimethylamino)phthalide, 3-di-n-hexylamino-6-(N-tert-butyl-N-tetrahydrofur-furylamino)fluorene-9-spiro-3'-(6'-diethylamino)phthalide, 3-di-n-hexylamino-6-(N-methyl-N-tetrahydrofur-furylamino)fluorene-9-spiro-3'-(6'-diethylamino)phthalide, 3-di-n-hexylamino-6-ditetrahydrofurfurylaminofluorene-9-spiro-3'-(6'-diethylamino)phthalide, 3-di-n-octylamino-6-(N-methyl-N-tetrahydrofur-furylamino)fluorene-9-spiro-3'-(6'-dimethylamino)phthalide, 3-(N-methyl-N-ethylamino)-6-(N-ethyl-N-tetrahydrofurfurylamino)fluorene-9-spiro-3'-(6'-dimethylamino)pthalide, 3-(N-ethyl-N-n-butylamino)-6-(N-methyl-N-tetrahydrofurfurylamino)fluorene-9-spiro-3'-(6'-dimethylamino)phthalide, 3-(N-ethyl-N-n-hexylamino)-6-(N-n-butyl-N-tetrahydrofurfurylamino)fluorene-9-spiro-3'-(6'-dipentylamino)phthalide, 3-ethylamino-6-(N-ethyl-N-tetrahydrofurfurylamino)fluorene-9-spiro-3'-(6'-dimethylamino)phthalide, 3-n-butylamino-6-ditetrahydrofurfurylaminofluorene-9-spiro-3'-(6'-dimethylamino)phthalide, 3-(N-tert-butyl-N-n-octylamino)-6-ditetrahydropyran-2-methylaminofluorene-9-spiro-3'-(6'-dimethylamino)phthalide, 3-amino-6-ditetrahydrofurfurylaminofluorene-9-spiro-3'-(6'-dimethylamino)phthalide, 3-amino-6-(N-methyl-N-tetrahydropyran-2-methylamino)fluorene-9-spiro-3'-(6'-diethylamino)phthalide, 3-(N-n-hexyl-N-n-octylamino)-6-(N-ethyl-N-tetrahydropyran-2-methylamino)fluorene-9-spiro-3'-(6'-diethylamino)phthalide,
3-(N-isoamyl-N-ethylamino)-6-(N-tetrahydropyran-2-methyl-N-propargylamino)fluorene-9-spiro-3'-(6'-diethylamino)phthalide,
3-morpholino-6-(N-methyl-N-tetrahydropyran-2-methylamino)fluorene-9-spiro-3'-(6'-diethylamino)phthalide,
3-morpholino-6-ditetrahydrofurfurylaminofluorene-9-spiro-3'-(6'-dimethylamino)phthalide,
3-pyrrolidino-6-(N-methyl-N-tetrahydrofurfurylamino)fluorene-9-spiro-3'-(6'-pyrrolidino)phthalide,
3-pyrrolidino-6-(N-ethyl-N-tetrahydrofurfurylamino)fluorene-9-spiro-3'-(6'-dimethylamino)phthalide,
3-pyrrolidino-6-(N-n-butyl-N-tetrahydrofurfurylamino)fluorene-9-spiro-3'-(6'-dibutylamino)phthalide,
3-pyrrolidino-6-ditetrahydrofurfurylaminofluorene-9-spiro-3'-(6'-diethylamino)phthalide,
3-piperidino-6-(N-methyl-N-tetrahydrofurfurylamino)fluorene-9-spiro-3'-(6'-dipropylamino)phthalide,
3-piperidino-6-(N-isopropyl-N-tetrahydrofurfurylamino)fluorene-9-spiro-3'-(6'-diethylamino)phthalide,
3-piperidino-6-(N-n-octyl-N-tetrahydropyran-2-methylamino)fluorene-9-spiro-3'-(6'-dibutylamino)phthalide,
3-hexamethyleneimino-6-(N-ethyl-N-tetrahydrofurfurylamino)fluorene-9-spiro-3'-(6'-dioctylamino)phthalide,
3-β-pipecolino-6-(N-ethyl-N-tetrahydrofurfurylamino)fluorene-9-spiro-3'-(6'-dimethylamino)phthalide,
3-(N-cyclohexyl-N-methylamino)-6-(N-methyl-N-tetrahydrofurfurylamino)fluorene-9-spiro-3'-(6'-diethylamino)phthalide,
3-(N-methyl-N-cyclohexylamino)-6-(N-ethyl-N-tetrahydropyran-2-methylamino)fluorene-9-spiro-3'-(6'-dimethylamino)phthalide,
3-(N-cyclopentyl-N-ethylamino)-6-(N-ethyl-N-tetrahydrofurfurylamino)fluorene-9-spiro-3'-(6'-dibutylamino)phthalide,
3-(N-3,3,5-trimethylcyclohexyl-N-ethylamino)-6-(N-ethyl-N-tetrahydrofurfurylamino)fluorene-9-spiro-3'-(6'-dimathylamino)phthalide,
3-(N-cyclododecyl-N-n-butylamino)-6-(N-methyl-N-tetrahydrofurfurylamino)fluorene-9-spiro-3'-(6'-diethylamino)phthalide,
3-(N-phenyl-N-methylamino)-6-(N-methyl-N-tetrahydrofurfurylamino)fluorene-9-spiro-3'-(6'-diethylamino)phthalide,
3-(N-p-tolyl-N-methylamino)-6-(N-methyl-N-tetrahydrofurfurylamino)fluorene-9-spiro-3'-(6'-diethylamino)phthalide,
3-(N-xylidyl-N-ethylamino)-6-(N-ethyl-N-tetrahydrofurfurylamino)fluorene-9-spiro-3'-(6'-diethylamino)phthalide,
3-(N-ethyl-p-chloroaniline)-6-(N-methyl-N-tetrahydrofurfurylamino)fluorene-9-spiro-3'-(6'-dibutylamino)phthalide,
3-(N-ethyl-p-tert-butylanilino)-6-(N-n-butyl-N-tetrahydrofurfurylamino)fluorene-9-spiro-3'-(6'-dimethylamino)phthalide,
3-(N-methyl-p-ethoxyanilino)-6-(N-methyl-N-tetrahydrofurfurylamino)fluorene-9-spiro-3'-(6'-dimethylamino)phthalide,
3-(N-methyl-N-benzylamino)-6-(N-isoamyl-N-tetrahydrofurfurylamino)fluorene-9-spiro-3'-(6'-dibutylamino)phthalide,
3-(N-methyl-N-chlorobenzylamino)-6-(N-n-propyl-N-tetrahydrofurfurylamino)fluorene-9-spiro-3'-(6'-dimethylamino)phthalide,
3-(N-n-propyl-N-m-ethylbenzylamino)-6-(N-n-amyl-N-tetrahydrofurfurylamino)fluorene-9-spiro-3'-(6'-diethylamino)phthalide,
3-(N-methyl-N-p-methoxybenzylamino)-6-(N-methyl-N-tetrahydrofurfurylamino)fluorene-9-spiro-3'-(6'-dimethylamino)phthalide,
3-(N-n-butyl-N-cyclohexylmethylamino)-6-(N-n-butyl-N-tetrahydropyran-2-methylamino)fluorene-9-spiro-3'-(6'-diethylamino)phthalide,
3-(N-isopropyl-N-phenylethylamino)-6-(N-methyl-N-tetrahydrofurfurylamino)fluorene-9-spiro-3'-(6'-dipropylamino)phthalide,
3,6-bis(N-ethyl-N-tetrahydrofurfurylamino)fluorene-9-spiro-3'-(6'-dimethylamino)phthalide,
3,6-bis(ditetrahydrofurfurylamino)fluorene-9-spiro-3'-(6'-dihexylamino)phthalide,
3,6-bis(N-phenyl-N-tetrahydrofurfurylamino)fluorene-9-spiro-3'-(6'-dimethylamino)phthalide,
3,6-bis(N-cyclohexyl-N-tetrahydrofurfurylamino)fluorene-9-spiro-3'-(6'-diethylamino)phthalide,
3-(N,N-dibutoxybutylamino)-6-(N-ethyl-N-tetrahydropyran-2-methylamino)fluorene-9-spiro-3'-(6'-diethylamino)phthalide,
3-(N-allyl-N-p-tolylamino)-6-(N-methyl-N-tetrahydropyran-2-methylamino)fluorene-9-spiro-3'-(6'-dimethylamino)phthalide,
3-(N-methoxypropyl-N-ethylamino)-6-(N-ethyl-N-tetrahydrofurfurylamino)fluorene-9-spiro-3'-(6'-dimethylamino)phthalide,
3-(N-ethoxybutyl-N-n-butylamino)-6-(N-allyl-N-tetrahydropyran-2-methylamino)fluorene-9-spiro-3'-(6'-dimethylamino)phthalide,
3-(N-butoxyethyl-N-propargylamino)-6-(N-tetrahydrofurfuryl-N-ethoxybutylamino)fluorene-9-spiro-3'-(6'-diethylamino)phthalide,
3-pyrrolidino-6-(N-tetrahydrofurfuryl-N-isopropoxyethylamino)fluorene-9-spiro-3'-(6'-pyrrolidino)phthalide,
3-(N-ethyl-N-methylamino)-6-(N-ethyl-N-tetrahydrofurfurylamino)fluorene-9-spiro-3'-(6'-pyrrolidino)phthalide,
3-(N-ethyl-N-p-tolylamino)-6-(N-methyl-N-tetrahydrofurfurylamino)fluorene-9-spiro-3'-(6'-piperidino)phthalide,
3-(N-methyl-N-ethoxyethylamino)-6-(N-ethyl-N-tetrahydrofurfurylamino)fluorene-9-spiro-3'-(6'-N-ethyl-p-chloroanilino)phthalide,
3,6-bis(N-ethyl-N-ethoxyethylamino)fluorene-9-spiro-3'-(6'-N-ethyl-N-tetrahydrofurfurylamino)phthalide,
3-dimethylamino-6-(N-methyl-N-tetrahydropyran-2-methylamino)fluorene-9-spiro-3'-(6'-N-n-butylamino)phthalide,
3-diethylamino-6-(N-n-pentyloxyethylamino)fluorene-9-spiro-3'-(6'-ditetrahydrofurfurylamino)phthalide,
3-dimethylamino-6-(N-ethyl-N-ethoxyethylamino)fluorene-9-spiro-3'-(6'-N-methyl-N-tetrahydropyran-2-methylamino)phthalide;
3-dimethylamino-6-(N-ethyl-N-β-phenylethylamino)fluorene-9-spiro-3'-(6'-dimethylamino)phthalide,
3-dimethylamino-6-(N-methyl-N-β-phenylethylamino)fluorene-9-spiro-3'-(6'-dimethylamino)phthalide, 3-diethylamino-6-(N-methyl-N-α-phenylethylamino)-fluorene-9-spiro-3'-(6'-dimethylamino)phthalide,
3-dimethylamino-6-(N-methyl-N-o-chlorobenzylamino)fluorene-9-spiro-3'-(6'-dimethylamino)phthalide,
3-diethylamino-6-(N-methyl-N-p-chlorobenzylamino)-fluorene-9-spiro-3'-(6'-dimethylamino)phthalide,
3-pyrrolidino-6-(N-ethyl-N-β-phenylethylamino)fluorene-9-spiro-3'-(6'-pyrrolidino)phthalide,
3-(di-n-butylamino)-6-(N-methyl-N-α-phenylethylamino)fluorene-9-spiro-3'-(6'-dimethylamino)phthalide;
3-dimethylamino-6-(N-methyl-N-phenoxyethylamino)-fluorene-9-spiro-3'-(6'-dimethylamino)phthalide,
3-diethylamino-6-(N-methyl-N-phenoxyethylamino)-fluorene-9-spiro-3'-(6'-dimethylamino)phthalide,
3-di-n-butylamino-6-(N-ethyl-N-p-methoxyphenoxyethylamino)fluorene-9-spiro-3'-(6'-dimethylamino)phthalide,
3-pyrrolidino-6-(N-methyl-N-p-chlorophenoxypropylamino)fluorene-9-spiro-3'-(6'-pyrrolidino)phthalide,
3-(N-methyl-N-cyclohexylamino)-6-(N-methyl-N-p-methylphenoxyethylamino)fluorene-9-spiro-3'-(6'-dimethylamino)phthalide;
3-dimethylamino-6-(N-ethyl-N-2-chloroethylamino)-fluorene-9-spiro-3'-(6'-dimethylamino)phthalide,
3-diethylamino-6-(N-methyl-N-2-chloroethylamino)-fluorene-9-spiro-3'-(6'-dimethylamino)phthalide,
3-di-n-butylamino-6-(N-ethyl-N-3-chloro-n-propylamino)fluorene-9-spiro-3'-(6'-dimethylamino)phthalide,
3-pyrrolidino-6-(N-methyl-N-2-bromoethylamino)fluorene-9-spiro-3'-(6'-pyrrolidino)phthalide,
3-(N-methyl-N-cyclohexylamino)-6-(N-methyl-N-bromo-n-butylamino)fluorene-9-spiro-3'-(6'-dimethylamino)phthalide and the like.

The phthalide derivatives according to the invention are substantially colorless chromogenic compounds having very superior properties. Especially, the phthalide derivatives are useful as chromogenic materials for producing record materials utilizing the colorforming reaction between a colorless chromogenic material and an electron accepting materials (hereinafter referred to as "acceptors").

Among the phthalide derivatives represented by the formula (I) according to the invention, those in which at least one of $R_1$, $R_2$, $R_3$, $R_4$, $R_5$ and $R_6$ is alkoxyalkyl having 3 to 4 carbon atoms, unsaturated alkyl having 3 to 4 carbon atoms or tetrahydrofurfuryl, particularly alkoxyalkyl having 3 to 4 carbon atoms or tetrahydrofurfuryl, are preferred, because the record materials prepared with the use of them are very superior in light resistance.

The phthalide derivatives according to the invention may be used either solely or in combination or, when desired, together with any of the following basic dye compounds: triarylmethanelactone compounds such as 3,3-bis(p-dimethylaminophenyl)-6-dimethylaminophthalide, 3-(p-dibenzylaminophenyl)-3-(1,2-dimethylindole-3-yl)-7-azaphthalide, 3-(4-diethylamino-2-ethoxyphenyl)-3-(1-ethyl-2-methylindole-3-yl)-7-azaphthalide and 3,3-bis(1-ethyl-2-methylindole-3-yl)phthalide; fluoran compounds such as 3-diethylamino-6-methylfluoran, 3-diethylamino-6-methyl-7-chlorofluoran, 3-(N-ethyl-N-p-tolylamino)-7-methylfluoran, 3-diethylamino-6-methyl-7-anilinofluoran, 3-(N-ethyl-N-i-pentylamino)-6-methyl-7-anilinofluoran, 3-(N-ethyl-N-tetrahydrofurfurylamino)-6-methyl-7-anilinofluoran, 3-(N-cyclohexyl-N-methylamino)-6-methyl-7-anilinofluoran, 3-(N-ethyl-N-p-tolylamino)-6-methyl-7-anilinofluoran, 3-diethylamino-6-chloro-7-anilinofluoran, 3-dibutylamino-7-o-chloroanilinofluoran and 3-dibutylamino-7-o-fluoroanilinofluoran; spiropyran compounds such as di-β-naphthospiropyran and 3-methyl-di-β-naphthospiropyran; diphenylmethane compounds such as 4,4'-bis-dimethylaminobenzhydrylbenzyl ether and 4,4'-bis-dimethylaminobenzhydryl-p-toluenesulfinic acid ester; azine compounds such as 3,7-bis(dimethylamino)-10-benzoylphenothiazine and 3,7-bis(diethylamino)-10-benzoylphenoxazine; and triarylmethane compounds such as N-butyl-3-[bis{4-(N-methylanilino)phenyl}methyl]carbazole.

The acceptors used are selected according to the kinds of record materials. The materials which are preferably used as acceptors for pressure sensitive record materials, heat sensitive record materials, electrothermal record materials, ultrasonic record materials, electrostatic record materials, typewriter's ribbons, ballpoint pen ink and crayon are those which function as Bronsted or Lewis acid. Among them there are included: inorganic acceptors such as acid clay, activated clay, attapulgite, bentonite, colloidal silica, aluminum silicate, magnesium silicate, zinc silicate, tin silicate, calcined kaolin and talc; organic acceptors such as aliphatic carboxylic acids, e.g., oxalic acid, maleic acid, tartaric acid, citric acid, succinic acid and stearic acid, aromatic carboxylic acids, e.g., benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-(α,α-dimethylbenzyl)salicylic acid, 3,5-di(α-methylbenzyl)-salicylic acid and 2-hydroxy-1-benzyl-3-naphthoic acid, phenolic compounds, e.g., 4,4'-isopropylidenediphenol, 4,4'-isopropylidenebis(2-chlorophenol), 4,4'-isopropylidenebis(2,6-dibromophenol), 4,4'-isopropylidenebis(2,6-dichlorophenol), 4,4'-isopropylidenebis(2-methylphenol), 4,4'-isopropylidenebis(2,6-dimethylphenol), 4,4'-isopropylidenebis(2-tert-butylphenol), 4,4'-sec-butylidenebisphenol, 4,4'-cyclohexylidenebisphenol, 4,4'-cyclohexylidenebis(2-methylphenol), 4-tert-butylphenol, 4-phenylphenol, 4-hydroxydiphenoxide, α-naphthol, β-naphthol, methyl 4-hydroxybenzoate, benzyl 4-hydroxybenzoate, 2,2'-thiobis(4,6-dichlorophenol), 4-tert-octylcatechol, 2,2'-methylenebis(4-chlorophenol), 2,2'-methylenebis(4-methyl-6-tert-butylphenol), 2,2'-dihydroxydiphenyl, 4-hydroxydiphenyl sulfone and 4-hydroxy-4'-methyldiphenyl sulfone, phenol resins, e.g., p-phenylphenol-formaldehyde resin and p-butylphenol-acetylene resin; salts of the above organic acceptors with polyvalent metals such as zinc, magnesium, aluminium, calcium, titanium, manganese, tin and nickel; and inorganic acid such as hydrogen halide, e.g., hydrogen chloride, hydrogen bromide and hydrogen iodide, boric acid, silicic acid, phosphoric acid, sulfuric acid, nitric acid, perchloric acid and halides of aluminium, zinc, nickel, tin, titanium, boron and the like.

In the case of electron beam record materials or photosensitive record materials, compounds which can produce by electron beam or light radiation hydrogen halogenides, such as hydrogen chloride, hydrogen bromide and hydrogen iodide, carboxylic acids, sulfonic acids or phenols are preferably used as acceptor materials. Among those compounds, there are included organic halogen compounds, such as carbon tetrabromide, α,α,α-tribromoacetophenone, hexachloroethane, iodoform, 2-tribromomethylpyridine, trichloromethyl sulfonylbenzene, o-quinonediazido compounds, phenol esters of carboxylic acid or sulfonic acid which can cause Fries rearrangement.

Some embodiments of the utilization of the phthalide derivatives according to the invention for various kinds of record materials are described hereinbelow:

The phthalide derivatives can be utilized for various kinds of pressure sensitive record materials, e.g., those disclosed in U.S. Pat. Nos. 2,505,470, 2,505,471, 2,505,489, 2,548,366, 2,712,507, 2,730,456, 2,730,457, 3,418,250, 3,924,027 and 4,010,038.

A typical method for the production of a pressure sensitive record material utilizing the phthalide derivatives according to the invention is as follows:

At least one of the phthalide derivatives according to the invention is dissolved in a solvent to form a solution which may include synthetic oil such as alkylated naphthalene, alkylated diphenyl, alkylated diphenylmethane and alkylated terphenyl, vegetable oil such as cotton seed oil and castor oil, animal oil and mineral oil or mixtures of the foregoing. The solution may additionally include basic colorless chromogenic material such as triarylmethane lactones, spiropyrans, fluorans, diphenylmethanes and azines. The solution of the phthalide derivative may be dispersed in a binder to form a coating composition. The solution may be enclosed in microcapsules through the utilization of the coacervation technique, the interfacial polymerization technique, the in-situ polymerization technique or any other method for making oil droplet-containing microcapsules and the microcapsules thus prepared are dispersed in a binder to form a coating composition. Any one of the coating compositions thus prepared is applied to a base sheet such as a paper sheet, plastic sheet, resin coated paper sheet, etc. to obtain a pressure sensitive record material. In case where the pressure sensitive copying system consists of a top sheet, a bottom sheet and, if necessary, at least one middle sheet, the pressure sensitive record material according to the invention is used as the top sheet and the middle sheet. The pressure sensitive record material according to the invention also be utilized in the "self contained" system in which both the colorless chromogenic material and the acceptor are dispersed on one surface of the same sheet. The pressure sensitive record material utilizing the phthalide derivative according to the invention can produce clear color images having a good light resistance and showing a good absorption for infrared rays which enables a certain reading by an optical reading machine.

The phthalide derivatives according to the invention are also useful for production of various kinds of heat sensitive record materials, e.g., as disclosed in Japanese Patent Pablications Nos. 3,680 of 1969, 27,880 of 1969, 14,039 of 1970, 43,830 of 1973, 69 of 1974, 70 of 1974 and 20,142 of 1977.

Most typically, heat sensitive record materials may be produced by coating a coating composition including fine particles of basic chromogenic material comprising the phthalide derivative according to the invention, an acceptor and a binder on a base sheet such as paper sheet, plastic film, synthetic paper sheet, woven fabric sheet or mold. The amount of the acceptor in the recording layer may be within the range of 1 to 50 parts by weight, preferably within the range of 2 to 10 parts by weight, per one part by weight of the basic chromogenic material use.

The coating composition may include inorganic metal compounds such as oxides, hydroxides and carbonates of polyvalent metals and/or inorganic pigments in an amount of 0.1 to 10 parts by weight, preferably, 0.5 to 3 parts by weight, per one part by weight of the amount of the acceptor. Further, the recording layer may also include dispersing agents, ultraviolet ray absorbing agents, heat fusible materials, antifoaming agent, fluorescent dye, coloring dyes and other adding materials. The phthalide derivative and the acceptor may be applied to a base sheet either in the form of a single coating composition or in the form of two separate coating compositions which may be applied one by one. Application of the phthalide derivative and acceptor to a base sheet may also be carried out by impregnation or by sizing. The amount of the coating composition including the phthalide derivative and the acceptor may preferably be within the range of 2 to 12 g/cm$^2$. Among the useful binder materials there may be included starches, celluloses, proteins, gum arabic, polyvinyl alcohol, salts of styrene-maleic anhydride copolymer, styrene-butadiene copolymer emulsions, salts of vinyl acetate-maleic anhydride copolymer and salts of polyacrylic acid.

The electrothermal record materials may be produced according to any known methods such as those disclosed in Japanese Laid-Open Patent Publications Nos. 11,344 of 1974 and 48,930 of 1975. Usually, the record material of this type may be produced, either by coating on a base sheet such as a paper sheet a coating composition essentially consisting of a dispersion of an electroconductive material, a basic chromogenic material comprising the phthalide derivative according to the invention, an acceptor and a binder, or by coating an electroconductive material on a base sheet to form an electroconductive layer thereon and further coating on the electroconductive layer another coating composition essentially consisting of a dispersion of the phthalide derivative according to the invention, an acceptor and a binder. In case where each of the phthalide derivative and the acceptor used is not fusible within the temperature range of 70° to 120° C., an appropriate heat fusible material may be added for controlling the heat sensitivity.

The photosensitive record materials in which the phthalide derivatives according to the invention are utilized may be produced in a similar manner to any of those disclosed in Japanese Patent Publications Nos. 24,188 to 1963, 10,550 of 1970, 13,258 of 1970, 204 of 1974, 6,212 of 1974 and 28,449 of 1974 and Japanese Laid-Open Patent Publications Nos. 31,615 of 1972, 32,532 of 1973, 9,227 of 1974, 135,617 of 1974, 80,120 of 1975, 87,317 of 1975 and 126,228 of 1975.

The invention is also applicable to other recording systems, such as, the ultrasonic record material, e.g., as disclosed in French Patent Specification No. 2,120,922, the electron beam recording system, e.g., as disclosed in Belgian Patent No. 7,959,986, the electrostatic record material, e.g., as disclosed in Japanese Patent Publication No. 3,932 of 1974, the photosensitive printing material, e.g., as disclosed in Japanese Laid-Open Patent Publication No. 12,104 of 1973, the seal stamping material, e.g., as disclosed in Japanese Patent Publication No. 10,766 of 1972, typewriter ribbons as disclosed in Japanese Laid-Open Patent Publication No. 3,713 of 1974, ball-point pen ink as disclosed in Japanese Laid- Open Patent Publication No. 83,924 of 1973 and crayon as disclosed in U.S. Pat. No. 3,769,045, by merely using the phthalide derivatives instead of the conventional basic colorless chromogenic materials.

PREFERRED EMBODIMENTS OF THE INVENTION

The following examples serve to illustrate the invention in more detail although the invention is not limited to the examples. Unless otherwise indicated, parts and % signify parts by weight and % by weight, respectively.

EXAMPLE 1

Preparation of
3-dimethylamino-6-(N-ethyl-N-ethoxyethylamino)fluorene-9-spiro-3'-(6'-dimethylamino)phthalide 10 g of 3-(2-amino-4-dimethylaminophenyl)-3-(4-N-ethyl-N-ethoxyethylaminophenyl)-6-dimethylaminophthalide was dissolved in 120 ml of 70% aqueous solution of sulphuric acid. To the obtained solution, a solution comprising 1.45 g of sodium nitrite in 23 ml of concentrated sulphuric acid was added dropwise at 0° to 5° C. for 30 minutes, and then the mixture was stirred at 5° C. for 30 minutes. 1.7 g of copper powder was added to the mixture and made to react at room temperature for one hour. The obtained reaction mixture was poured into 2 l of water and neutralized with sodium hydroxide. The resultant precipitate was filtered off and recrystallized from ethanol/water to obtain white crystals in a 82% yield (8 g). The phthalide derivative had a melting point of 145° to 147° C. and became blue upon contact with silica gel.

EXAMPLE 2

Preparation of
3-dimethylamino-6-(N-ethyl-N-methoxyethylamino)-fluorene-9-spiro-3'-(6'-dimethylamino)phthalide 10 g of 3-(2-amino-4-dimethylaminophenyl)-3-(4-N-ethyl-N-methoxyethylaminophenyl)-6-dimethylaminophthalide was dissolved in 100 ml of 70% aqueous solution of sulphuric acid at a low temperature. To the obtained solution, a solution comprising 1.46 g of sodium nitrite in 25 ml of concentrated sulphuric acid was added dropwise for 30 minutes under cooling in ice bath, and then the mixture was stirred at the same temperature for 30 minutes. 1.7 g of copper powder was added to the mixture and made to react under cooling in ice bath for 2 hours. The obtained reaction mixture was poured into 2 l of water and neutralized with sodium hydroxide. The resultant precipitate was filtered off and recrystallized from ethanol to obtain white crystals in a 77.8% yield (7.5 g). The phthalide derivative had a melting point of 162° to 167° C. and became blue upon contact with silica gel.

EXAMPLE 3

Preparation of
3-di-n-butylamino-6-(N-methyl-N-methoxyethylamino)fluorene-9-spiro-3'-(6'-dimethylamino)phthalide Example 1 was repeated except that 5.6 g of 3-(2-amino-4-di-n-butylaminophenyl)-3-(4-N-methyl-N-methoxyethylaminophenyl)-6-dimethylaminophthalide was used instead of 3-(2-amino-4-dimethylaminophenyl)-3-(4-N-ethyl-N-ethoxyethylaminophenyl)-6-dimethylaminophthalide to obtain white crystals having a melting point of 115° to 119° C. in a 71% yield (3.85 g). The phthalide derivative became blue upon contact with silica gel.

EXAMPLE 4

Preparation of
3-pyrrolidino-6-(N-ethyl-N-ethoxyethylamino)fluorene-9-spiro-3'-(6'-pyrrolidino)phthalide Example 1 was repeated except that 11 g of 3-(2-amino-4-pyrrolidinophenyl)-3-(4-N-ethyl-N-ethoxyethylaminophenyl)-6-pyrrolidinophthalide was used instead of 3-(2-amino-4-dimethylaminophenyl)-3-(4-N-ethyl-N-ethoxyethylaminophenyl)-6-dimethylaminophthalide to obtain white crystals having a melting point of 150° to 155° C. in a 73% yield (7.8 g). The phthalide derivative became blue upon contact with silica gel.

EXAMPLE 5

Preparation of
3-(N-methyl-N-cyclohexylamino)-6-(N-ethyl-N-ethoxyethylamino)fluorene-9-spiro-3'-(6'-dimethylamino)phthalide Example 1 was repeated except that 11.4 g of 3-(2-amino-4-N-methyl-N-cyclohexylaminophenyl)-3-(4-N-ethyl-N-ethoxyethylaminophenyl)-6-dimethylaminophthalide was used instead of 3-(2-amino-4-dimethylaminophenyl)-3-(4-N-ethyl-N-ethoxyethylaminophenyl)-6-dimethylaminophthalide to obtain white crystals having a melting point of 148° to 152° C. in a 75% yield (8.3 g). The phthalide derivative became blue upon contact with silica gel.

EXAMPLE 6

Preparation of
3-dimethylamino-6-(N-methyl-N-methoxyethylamino)-fluorene-9-spiro-3'-(6'-dimethylamino)phthalide Example 1 was repeated except that 10.0 g of 3-(2-amino-4-dimethylaminophenyl)-3-(4-N-methyl-N-methoxyethylaminophenyl)-6-dimethylaminophthalide was used instead of 3-(2-amino-4-dimethylaminophenyl)-3-(4-N-ethyl-N-ethoxyethylaminophenyl)-6-dimethylaminophthalide to obtained white crystals having a melting point of 140° to 143° C. in a 75% yield (7.2 g). The phthalide derivative became blue upon contact with silica gel.

EXAMPLE 7

Preparation of
3-diethylamino-6-(N-methyl-N-methoxyethylamino)-fluorene-9-spiro-3'-(6'-dimethylamino)phthalide Example 1 was repeated except that 6.0 g of 3-(2-amino-4-diethylaminophenyl)-3-(4-N-methyl-N-methoxyethylaminophenyl)-6-dimethylaminophthalide was used instead of 3-(2-amino-4-dimethylaminophenyl)-3-(4-N-ethyl-N-ethoxyethylaminophenyl)-6-dimethylaminophthalide to obtain white crystals having a melting point of 137° to 141° C. in a 73% yield (4.2 g). The phthalide derivative became blue upon contact with silica gel.

EXAMPLE 8

Preparation of
3-diethylamino-6-(N-ethyl-N-ethoxyethylamino)fluorene-9-spiro-3'-(6'-dimethylamino)phthalide Example 1 was repeated except that 6.0 g of 3-(2-amino-4-diethylaminophenyl)-3-(4-N-ethyl-N-ethoxyethylaminophenyl)-6-dimethylaminophthalide was used instead of 3-(2-amino-4-dimethylaminophenyl)-3-(4-N-ethyl-N-ethoxyethylaminophenyl)-6-dimethylaminophthalide to obtain white crystals having a melting point of 141° to 143° C. in a 76% yield (4.4 g). The phthalide derivative became blue upon contact with silica gel.

EXAMPLE 9

Preparation of
3-diethylamino-6-(N-methyl-N-allylamino)fluorene-9-spiro-3'-(6'-dimethylamino)phthalide 10 g of 3-(2-amino-4-diethylaminophenyl)-3-(4-N-methyl-N-allylaminophenyl)-6-dimethylaminophthalide was dissolved in 120 ml of 70% aqueous solution of sulphuric acid. To the obtained solution, a solution comprising 1.45 g of sodium nitrite in 23 ml of concentrated sulphuric acid was added dropwise at 0° to 5° C. for 30 minutes, and then the mixture was stirred at 5° C. for 30 minutes. 1.7 g of copper powder was added to the mixture and made to react at room temperature for 4 hours. The obtained reaction mixture was poured into 2 l of water and neutralized with sodium hydroxide. The resultant precipitate was filtered off and recrystallized from ethanol/water to obtain white crystals in a 76% yield (7.3 g). The phthalide derivative had a melting point of 161° to 165° C. and became blue upon contact with silica gel.

EXAMPLE 10

Preparation of
3-dimethylamino-6-(diallylamino)fluorene-9-spiro-3'-(6'-dimethylamino)phthalide 10 g of 3-(2-amino-4-dimethylaminophenyl)-3-(4-diallylaminophenyl)-6-dimethylaminophthalide was dissolved in 100 ml of 70% aqueous solution of sulphuric acid at a low temperature. To the obtained solution, a solution comprising 1.46 g of sodium nitrite in 25 ml of concentrated sulphuric acid was added dropwise for 30 minutes under cooling in ice bath, and then the mixture was stirred at the same temperature for 30 minutes. 1.7 g of copper powder was added to the mixture, made to react under cooling in ice bath for 2 hours, and then heated at 60° C. for 5 hours with stirring. The obtained reaction mixture was poured into 2 l of water and neutralized with sodium hydroxide. The resultant precipitate was filtered off and recrystallized from ethanol to obtain white crystals in a 67.4% yield (6.5 g). The phthalide derivative had a melting point of 219° to 221° C. and became blue upon contact with silica gel.

EXAMPLE 11

Preparation of
3-di-n-butylamino-6-(N-methyl-N-allylamino)fluorene-9-spiro-3'-(6'-dimethylamino)phthalide Example 9 was repeated except that 6.0 g of 3-(2-amino-4-di-n-butylaminophenyl)-3-(4-N-methyl-N-allylaminophenyl)-6-dimethylaminophthalide was used instead of 3-(2-amino-4-diethylaminophenyl)-3-(4-N-methyl-N-allylaminophenyl)-6-dimethylaminophthalide to obtain white crystals in a 63.6% yield (3.7 g). The phthalide derivative had a melting point of 122° to 126.5° C. and became blue upon contact with silica gel.

EXAMPLE 12

Preparation of
3-pyrrolidino-6-(N-ethyl-N-2-butenylamino)fluorene-9-spiro-3'-(6'-pyrrolidino)phthalide Example 9 was repeated except that 11 g of 3-(2-amino-4-pyrrolidinophenyl)-3-(4-ethyl-N-2-butenylaminophenyl)-6-pyrrolidinophthalide was used instead of 3-(2-amino-4-diethylaminophenyl)-3-(4-N-methyl-N-allylaminophenyl)-6-dimethylaminophthalide to obtain white crystals in a 76% yield (8.1 g). The phthalide derivative had a melting point of 158° to 162° C. and became blue upon contact with silica gel.

EXAMPLE 13

Preparation of
3-(N-methyl-N-cyclohexylamino)-6-(N-ethyl-N-propargylamino)fluorene-9-spiro-3'-(6'-dimethylamino)phthalide Example 10 was repeated except that 9 g of 3-(2-amino-4-N-methyl-N-cyclohexylaminophenyl)-3-(4-N-ethyl-N-propargylaminophenyl)-6-dimethylaminophthalide was used instead of 3-(2-amino-4-dimethylaminophenyl)-3-(4-diallylaminophenyl)-6-dimethylaminophthalide to obtain white crystals in a 86% yield (7.5 g). The phthalide derivative had a melting point of 171° to 174° C. and became blue upon contact with silica gel.

EXAMPLE 14

Preparation of
3-dimethylamino-6-(N-methyl-N-allylamino)fluorene-9-spiro-3'-(6'-dimethylamino)phthalide Example 9 was repeated except that 5.0 g of 3-(2-amino-4-dimethylaminophenyl)-3-(4-N-methyl-N-allylaminophenyl)-6-dimethylaminophthalide was used instead of 3-(2-amino-4-diethylaminophenyl)-3-(4-N-methyl-N-allylaminophenyl)-6-dimethylaminophthalide to obtain white crystals having a melting point of 191° to 193° C. in a yield of 77% (3.7 g). The phthalide derivative became blue upon contact with silica gel.

EXAMPLE 15

Preparation of
3-dimethylamino-6-(N-methyl-N-2-butenylamino)fluorene-9-spiro-3'-(6'-dimethylamino)phthalide Example 9 was repeated except that 5.0 g of 3-(2-amino-4-dimethylaminophenyl)-3-(4-N-methyl-N-2-butenylaminophenyl)-6-dimethylaminophthalide was used instead of 3-(2-amino-4-diethylaminophenyl)-3-(4-N-methyl-N-allylaminophenyl)-6-dimethylaminophthalide to obtain white crystals having a melting point of 183° to 187° C. in a yield of 73% (3.5 g). The phthalide derivative became blue upon contact with silica gel.

EXAMPLE 16

Preparation of
3-dimethylamino-6-(N-methyl-N-tetrahydrofurfurylamino)fluorene-9-spiro-3'-(6'-dimethylamino)phthalide 10 g of 3-(2-amino-4-dimethylaminophenyl)-3-(4-N-methyl-N-tetrahydrofurfurylaminophenyl)-6-dimethylaminophthalide was dissolved in 60 ml of 70% aqueous solution of sulphuric acid. To the obtained solution, a solution comprising 1.65 g of sodium nitrite in 23 ml of concentrated sulphuric acid was added dropwise at 0° to 5° C. for 30 minutes, and then the mixture was stirred at 5° C. for 30 minutes. 3.4 g of copper powder was added to the mixture and made to react at room temperature for 3 hours. The obtained reaction mixture was poured into 1 l of water and neutralized with sodium hydroxide. The resultant precipitate was filtered off and recrystallized from methanol to obtain white crystals in a 80% yield (7.7 g). The phthalide derivative had a melting point of 184° to 191° C. and became blue upon contact with silica gel.

EXAMPLE 17

Preparation of 3-diethylamino-6-(N-ethyl-N-tetrahydrofurfurylamino)fluorene-9-spiro-3'-(6'-dimethylamino)phthalide 10 g of 3-(2-amino-4-diethylaminophenyl)-3-(4-N-ethyl-N-tetrahydrofurfurylaminophenyl)-6-dimethylaminophthalide was dissolved in 100 ml of 70% aqueous solution of sulphuric acid at a low temperature. To the obtained solution, a solution comprising 1.52 g of sodium nitrite in 25 ml of concentrated sulphuric acid was added dropwise for 30 minutes under cooling in ice bath, and then the mixture was stirred at the same temperature for 30 minutes. 1.7 g of copper power was added to the mixture and made to react under cooling in ice bath for 4 hours. The obtained reaction mixture was poured into 1 l of water and neutralized with sodium hydroxide. The resultant precipitate was filtered off and recystallized from ethanol to obtain white crystals in a 76.4% yield (7.4 g). The phthalide derivative had a melting point of 155° to 160° C. and became blue upon contact with silica gel.

EXAMPLE 18

Preparation of 3-di-n-butylamino-6-(N-methyl-N-tetrahydrofurfurylamino)fluorene-9-spiro-3'-(6'-dimethylamino)phthalide Example 16 was repeated except that 5.8 g of 3-(2-amino-4-di-n-butylaminophenyl)-3-(4-N-methyl-N-tetrahydrofurfurylaminophenyl)-6-dimethylaminophthalide was used instead of 3-(2-amino-4-dimethylaminophenyl)-3-(4-N-methyl-N-tetrahydrofurfurylaminophenyl)-6-dimethylaminophthalide to obtain white crystals in a 77% yield (4.33 g). The phthalide derivative had a melting point of 136° to 140° C. and became blue upon contact with silica gel.

EXAMPLE 19

Preparation of 3-pyrrolidino-6-(N-methyl-N-tetrahydrofurfurylamino)fluorene-9-spiro-3'-(6'-pyrrolidino)phthalide Example 16 was repeated except that 11 g of 3-(2-amino-4-pyrrolidinophenyl)-3-(4-N-methyl-N-tetrahydrofurfurylaminophenyl)-6-pyrrolidinophthalide was used instead of 3-(2-amino-4-dimethylaminophenyl)-3-(4-N-methyl-N-tetrahydrofurfurylaminophenyl)-6-dimethylaminophthalide to obtain white crystals in a 74% yield (7.9 g). The phthalide derivative had a melting point of 165° to 170° C. and became blue upon contact with silica gel.

EXAMPLE 20

Preparation of 3-(N-methyl-N-cyclohexylamino)-6-(N-ethyl-N-tetrahydropyran-2-methylamino)fluorene-9-spiro-3'-(6'-dimethylamino)phthalide Example 16 was repeated except that 11.6 g of 3-(2-amino-4-N-methyl-N-cyclohexylaminophenyl)-3-(4-N-ethyl-N-tetrahydropyran-2-methylaminophenyl)-6-dimethylaminophthalide was used instead of 3-(2-amino-4-dimethylaminophenyl)-3-(4-N-methyl-N-tetrahydrofurfurylaminophenyl)-6-dimethylaminophthalide to obtain white crystals in a 75% yield (8.5 g). The phthalide derivative had a melting point of 157° to 162° C. and became blue upon contact with silica gel.

EXAMPLE 21

Preparation of 3-dimethylamino-6-(N-ethyl-N-tetrahydrofurfurylamino)fluorene-9-spiro-3'-(6'-dimethylamino)phthalide Example 16 was repeated except that 10.0 g of 3-(2-amino-4-dimethylaminophenyl)-3-(4-N-ethyl-N-tetrahydrofurfurylaminophenyl)-6-dimethylaminophthalide was used instead of 3-(2-amino-4-dimethylaminophenyl)-3-(4-N-methyl-N-tetrahydrofurfurylaminophenyl)-6-dimethylaminophthalide to obtain white crystals having a melting point of 207° to 209° C. in a yield of 76% (7.3 g). The phthalide derivative became blue upon contact with silica gel.

EXAMPLE 22

Preparation of 3-diethylamino-6-(N-methyl-N-tetrahydrofurfurylamino)fluorene-9-spiro-3'-(6'-dimethylamino)phthalide Example 16 was repeated except that 10.0 g of 3-(2-amino-4-N-diethylaminophenyl)-3-(4-N-methyl-N-tetrahydrofurfurylaminophenyl)-6-dimethylaminophthalide was used instead of 3-(2-amino-4-dimethylaminophenyl)-3-(4-N-methyl-N-tetrahydrofurfurylaminophenyl)-6-dimethylaminophthalide to obtain white crystals having a melting point of 203° to 205° C. in a yield of 74% (7.15 g). The phthalide derivative became blue upon contact with silica gel.

EXAMPLE 23

Preparation of 3-dimethylamino-6-(N-ethyl-N-$\beta$-phenylethylamino)-fluorene-9-spiro-3'-(6'-dimethylamino)phthalide 10 g of 3-(2-amino-4-dimethylaminophenyl)-3-(4-N-ethyl-N-$\beta$-phenylethylaminophenyl)-6-dimethylaminophthalide was dissolved in 120 ml of 70% aqueous solution of sulphuric acid. To the obtained solution, a solution comprising 1.35 g of sodium nitrite in 20 ml of concentrated sulphuric acid was added dropwise at 0° to 5° C. for 30 minutes, and then the mixture was stirred at 5° C. for 30 minutes. 1.5 g of copper powder was added to the mixture and made to react at room temperature for one hour. The obtained reaction mixture was poured into 2 l of water and neutralized with sodium hydroxide. The resultant precipitate was filtered off and recrystallized from ethanol to obtain white crystals in a 78.5% yield (7.6 g). The phthalide derivative had a melting point of 133° to 137° C. and became blue upon contact with silica gel.

EXAMPLE 24

Preparation of
3-diethylamino-6-(N-methyl-N-α-phenylethylamino)-fluorene-9-spiro-3'-(6'-dimethylamino)phthalide 10 g of 3-(2-amino-4-diethylaminophenyl)-3-(4-N-methyl-N-α-phenylethylaminophenyl)-6-dimethylaminophthalide was dissolved in 100 ml of 70% aqueous solution of sulphuric acid at a low temperature. To the obtained solution, a solution comprising 1.4 g of sodium nitrite in 25 ml of concentrated sulphuric acid was added dropwise for 30 minutes under cooling in ice bath, and then the mixture was stirred at the same temperature for 30 minutes. 1.7 g of copper powder was added to the mixture, made to react under cooling in ice bath for 2 hours, and then heated at 70° C. for 5 hours with stirring. The obtained reaction mixture was poured into 2 l of water and neutralized with sodium hydroxide. The resultant precipitate was filtered off and recrystalized from ethanol to obtain white crystals in a 82.6% yield (8 g). The phthalide derivative had a melting point of 184° to 186.5° C. and became blue upon contact with silica gel.

EXAMPLE 25

Preparation of
3-diethylamino-6-(N-methyl-N-p-chlorobenzylamino)-fluorene-9-spiro-3'-(6'-dimethylamino)phthalide Example 23 was repeated except that 11.4 g of 3-(2-amino-4-diethylaminophenyl)-3-(4-N-methyl-N-p-chlorobenzylaminophenyl)-6-dimethylaminophthalide was used instead of 3-(2-amino-4-dimethylaminophenyl)-3-(4-N-ethyl-N-β-phenylethylaminophenyl)-6-dimethylaminophthalide to obtain white crystals in a 71.2% yield (7.9 g). The phthalide derivative had a melting point of 187.5° to 189.5° C. and became blue upon contact with silica gel.

EXAMPLE 26

Preparation of
3-pyrrolidino-6-(N-ethyl-N-β-phenylethylamino)fluorene-9-spiro-3'-(6'-pyrrolidino)phthalide Example 38 was repeated except that 11 g of 3-(2-amino-4-pyrrolidinophenyl)-3-(4-N-ethyl-N-β-phenylethylaminophenyl)-6-pyrrolidinophthalide was used instead of 3-(2-amino-4-dimethylaminophenyl)-3-(4-N-β-phenylethylaminophenyl)-6-dimethylaminophthalide to obtain white crystals in a 72.1% yield (7.0 g). The phthalide derivative had a melting point of 144° to 148° C. and became blue upon contact with silica gel.

EXAMPLE 27

Preparation of
3-(di-n-butylamino)-6-(N-methyl-N-α-phenylethylamino)fluorene-9-spiro-3'-(6'-dimethylamino)phthalide Example 24 was repeated except that 6.5 g of 3-(2-amino-4-di-n-butylaminophenyl)-3-(4-N-methyl-N-α-phenylethylaminophenyl)-6-diethylaminophthalide was used instead of 3-(2-amino-4-diethylaminophenyl)-3-(4-N-methyl-N-α-phenylethylaminophenyl)-6-dimethylaminophthalide to obtain white crystals in a 64.9% yield (4.1 g). The phthalide derivative had a melting point of 120° to 124° C. and became blue upon contact with silica gel.

EXAMPLE 28

Preparation of
3-dimethylamino-6-(N-methyl-N-phenylethylamino)-fluorene-9-spiro-3'-(6'-dimethylamino)phthalide Example 23 was repeated except that 6.0 g of 3-(2-amino-4-dimethylaminophenyl)-3-(4-N-methyl-N-phenylethylaminophenyl)-6-dimethylaminophthalide was used instead of 3-(2-amino-4-diethylaminophenyl)-3-(4-N-ethyl-N-β-phenylethylaminophenyl)-6-dimethylaminophthalide to obtain white crystals having a melting point of 179° to 183° C. in a yield of 79% (4.6 g). The phthalide derivative became blue upon contact with silica gel.

EXAMPLE 29

Preparation of
3-dimethylamino-6-(N-methyl-N-o-chlorobenzylamino)fluorene-9-spiro-3'-(6'-dimethylamino)phthalide Example 23 was repeated except that 6.0 g of 3-(2-amino-4-dimethylaminophenyl)-3-(4-N-methyl-N-o-chlorobenzylaminophenyl)-6-dimethylaminophthalide was used instead of 3-(2-amino-4-diethylaminophenyl)-3-(4-N-ethy-N-β-phenylethylaminophenyl)-6-dimethylaminophthalide to obtain white crystals having a melting point of 215° to 218° C. in a yield of 77% (4.45 g). The phthalide derivative became blue upon contact with silica gel.

EXAMPLE 30

Preparation of
3-dimethylamino-6-(N-methyl-N-phenoxyethylamino)-fluorene-9-spiro-3'-(6'-dimethylamino)phthalide 10 g of 3-(2-amino-4-dimethylaminophenyl)-3-(4-N-methyl-N-phenoxyethylaminophenyl)-6-dimethylaminophthalide was dissolved in 60 ml of 70% aqueous solution of sulphuric acid. To the obtained solution, a solution comprising 1.54 g of sodium nitrite in 23 ml of concentrated sulphuric acid was added dropwise at 0° to 5° C. for 30 minutes, and then the mixture was stirred at 5° C. for 30 minutes. 1.7 g of copper powder was added to the mixture and made to react at room temperature for one hour. The obtained reaction mixture was poured into 1 l of water and neutralized with sodium hydroxide. The resultant precipitate was filtered off and recrystallized from ethanol to obtain white crystals in a 77% yield (7.45 g). The phthalide derivative had a melting point of 183° to 185° C. and became blue upon contact with silica gel.

EXAMPLE 31

Preparation of
3-diethylamino-6-(N-methyl-N-phenoxyethylamino)-fluorene-9-spiro-3'-(6'-dimethylamino)phthalide 10 g of 3-(2-amino-4-diethylaminophenyl)-3-(4-N-methyl-N-phenoxyethylaminophenyl)-6-dimethylaminophthalide was dissolved in 60 ml of 70% aqueous solution of sulphuric acid at a low temperature. To the obtained solution, a solution comprising 1.46 g of sodium nitrite in 22 ml of concentrated sulphuric acid was added dropwise for 30 minutes under cooling in ice bath, and then the mixture was stirred at the same temperature for 30 minutes. 1.7 g of copper powder was added to the mixture and made to react under cooling in ice bath for 2 hours. The obtained reaction mixture was poured into 1 l of water and neutralized with sodium hydroxide. The resultant precipitate was filtered off and recrystallized from n-butanol to obtain white crystals in a 75.3% yield (7.3 g). The phthalide derivative had a melting point of 194° to 196° C. and became blue upon contact with silica gel.

EXAMPLE 32

Preparation of
3-di-n-butylamino-6-(N-ethyl-N-p-methoxyphenoxyethylamino)fluorene-9-spiro-3'-(6'-dimethylamino)phthalide Example 30 was repeated except that 6.6 g of 3-(2-amino-4-di-n-butylaminophenyl)-3-(4-N-ethyl-N-p-methoxyphenoxyethylaminophenyl)-6-dimethylaminophthalide was used instead of 3-(2-amino-4-dimethylaminophenyl)-3-(4-N-methyl-N-phenoxyethylaminophenyl)-6-dimethylaminophthalide to obtain white crystals in a 72% yield (4.63 g). The phthalide derivative had a melting point of 121° to 125° C. and became blue upon contact with silica gel.

EXAMPLE 33

Preparation of
3-pyrrolidino-6-(N-methyl-N-p-chlorophenoxypropylamino)fluorene-9-spiro-3'-(6-pyrrolidino)phthalide Example 30 was repeated except that 6.1 g of 3-(2-amino-4-pyrrolidinophenyl)-3-(4-N-methyl-N-p-chlorophenoxypropylaminophenyl)-6-pyrrolidinophthalide was used instead of 3-(2-amino-4-dimethylaminophenyl)-3-(4-N-methyl-N-phenoxyethylaminophenyl)-6-dimethylaminophthalide to obtain white crystals in a 74% yield (4.4 g). The phthalide derivative had a melting point of 145° to 150° C. and became blue upon contact with silica gel.

EXAMPLE 34

Preparation of
3-(N-methyl-N-cyclohexylamino)-6-(N-methyl-N-p-methylphenoxyethylamino)fluorene-9-spiro-3'-(6'-dimethylamino)phthalide Example 30 was repeated except that 12.6 g of 3-(2-amino-4-N-methyl-N-cyclohexylaminophenyl)-3-(4-N-methyl-N-p-methylphenoxyethylaminophenyl)-6-dimethylaminophthalide was used instead of 3-(2-amino-4-dimethylaminophenyl)-3-(4-N-methyl-N-phenoxyethylaminophenyl)-6-dimethylaminophthalide to obtain white crystals in a 69% yield (8.4 g). The phthalide derivative had a melting point of 132° to 136° C. and became blue upon contact with silica gel.

EXAMPLE 35

Preparation of
3-dimethylamino-6-(N-ethyl-N-2-chloroethylamino)-fluorene-9-spiro-3'-(6'-dimethylamino)phthalide 2 g of 3-(4-dimethylaminophenyl)-3-(4-N-methyl-N-2-chloroethylaminophenyl)-6-dimethylaminophthalide was added to a melted mixture of 15.6 g of aluminum chloride and 2.34 g of urea and the resultant mixture was heated at 150° C. for 16 hours with stirring. After cooling, ice was added to the mixture to decompose aluminum chloride and then the mixture was made basic with an aqueous solution of sodium hydroxide. The resultant precipitate was filtered off and recrystallized from ethanol to obtain white crystals in a 60% yield (1.2 g). The phthalide derivative had a melting point of 259° to 262° C. and became blue upon contact with silica gel.

EXAMPLE 36

Preparation of
3-diethylamino-6-(N-methyl-N-2-chloroethylamino)-fluorene-9-spiro-3'-(6'-dimethylamino)phthalide 2 g of 3-(4-diethylaminophenyl)-3-(4-N-methyl-N-2-chloroethylaminophenyl)-6-dimethylaminophthalide was added to a mixture of 11.1 g of aluminum chloride and 2.3 g of urea and the resultant mixture was heated at 160° C. for 15 hours with stirring. After cooling, ice was added to the mixture to decompose aluminum chloride and then the mixture was made basic with an aqueous solution of sodium hydroxide. The resultant precipitate was filtered off and recrystallized from ethanol to obtain white crystals in a 62% yield (1.23 g). The phthalide derivative had a melting point of 205° to 210° C. and became blue upon contact with silica gel.

EXAMPLE 37

Preparation of
3-di-n-butylamino-6-(N-ethyl-N-3-chloro-n-propylamino)fluorene-9-spiro-3'-(6'-dimethylamino)phthalide Example 35 was repeated except that 6.0 g of 3-(4-di-n-butylaminophenyl)-3-(4-N-ethyl-N-3-chloro-n-propylaminophenyl)-6-dimethylaminophthalide was used instead of 3-(4-dimethylaminophenyl)-3-(4-N-methyl-N-2-chloroethylaminophenyl)-6-dimethylaminophthalide to obtain 3.2 g of white crystals having a melting point of 153° to 158° C. in 53% yield. The phthalide derivatives became blue upon contact with silica gel.

EXAMPLE 38

Preparation of
3-pyrrolidino-6-(N-methyl-N-2-bromoethylamino)fluorene-9-spiro-3'-(6'-pyrrolidino)phthalide Example 35 was repeated except that 5.4 g of 3-(4-pyrrolidinophenyl)-3-(4-N-methyl-N-2-bromoethylaminophenyl)-6-pyrrolidinophthalide was used instead of 3-(4-dimethylaminophenyl)-3-(4-N-methyl-N-2-chloroethylaminophenyl)-6-dimethylaminophthalide to obtain 3.3 g of white crystals having a melting point of 171° to 177° C. in 61% yield. The phthalide derivatives became blue upon contact with silica gel.

EXAMPLE 39

Preparation of
3-(N-methyl-N-cyclohexylamino)-6-(N-methyl-N-4-bromo-n-butylamino)fluorene-9-spiro-3'-(6'-dimethylamino)phthalide Example 35 was repeated except that 11.3 g of 3-(4-N-methyl-N-cyclohexylaminophenyl)-3-(4-N-methyl-N-4-bromo-n-butylaminophenyl)-6-dimethylaminophthalide was used instead of 3-(4-dimethylaminophenyl)-3-(4-N-methyl-N-2-chloroethylaminophenyl)-6-dimethylaminophthalide to obtain 5.9 g of white crystals having a melting point of 157° to 162° C. in 52% yield. The phthalide derivatives became blue upon contact with silica gel.

EXAMPLE 40

A heat-sensitive record material was prepared by the following method with the use of 3-dimethylamino-6-

(N-ethyl-N-ethoxyethylamino)fluorene-9-spiro-3'-(6'-dimethylamino)phthalide obtained in Example 1.

(1) Preparation of A liquid:

The following composition was passed through a sand mill.
- phthalide derivative obtained in Example 1: 10 parts
- 5% aqueous solution of methylcellulose: 5 parts
- water: 40 parts Pulverization was continued until an average particle size of 3 μm.

(2) Preparation of B liquid:

The following composition was passed through a sand mill.
- 4,4'-isopropylidene diphenol: 20 parts
- 5% aqueous solution of methylcellulose: 5 parts
- water: 55 parts Pulverization was continued until an average particle size of 3 μm.

(3) Preparation of C liquid:

The following composition was passed through a sand mill.
- stearic acid amide: 20 parts
- 5% aqueous solution of methylcellulose: 5 parts
- water: 55 parts Pulverization was continued until an average particle size of 3 μm.

(4) Making a heat-sensitive record material:

The following composition was mixed to prepare a coating composition.
- A liquid: 55 parts
- B liquid: 80 parts
- C liquid: 80 parts
- silicone dioxide pigment (oil absorption: 180 ml/100 g): 15 parts
- 20% aqueous solution of oxidized starch: 50 parts
- water: 10 parts The coating composition was coated on a base sheet of 50 mg/m² in the weight of an amount of 6 g/m² on dry basis to obtain a heat-sensitive record material.

EXAMPLE 41

Example 40 was repeated except that 3-dimethylamino-6-(N-ethyl-N-methoxyethylamino)fluorene-9-spiro-3'-(6'-dimethylamino)phthalide obtained in Example 2 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 42

Example 40 was repeated except that 3-di-n-butylamino-6-(N-methyl-N-methoxyethylamino)fluorene-9-spiro-3'-(6'-dimethylamino)phthalide obtained in Example 3 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 43

Example 40 was repeated except that 3-pyrrolidino-6-(N-ethyl-N-ethoxyethylamino)fluorene-9-spiro-3'-(6'-pyrrolidino)phthalide obtained in Example 4 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 44

Example 40 was repeated except that 3-diethylamino-6-(N-methyl-N-allylamino)fluorene-9-spiro-3'-(6'-dimethylamino)phthalide obtained in Example 9 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 45

Example 40 was repeated except that 3-dimethylamino-6-(diallylamino)fluorene-9-spiro-3'-(6'-dimethylamino)phthalide obtained in Example 10 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 46

Example 40 was repeated except that 3-di-n-butylamino-6-(N-methyl-N-allylamino)fluorene-9-spiro-3'-(6'-dimethylamino)phthalide obtained in Example 11 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 47

Example 40 was repeated except that 3-pyrrolidino-6-(N-ethyl-N-2-butenylamino)fluorene-9-spiro-3'-(6'-pyrrolidino)phthalide obtained in Example 12 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 48

Example 40 was repeated except that 3-dimethylamino-6-(N-methyl-N-tetrahydrofurfurylamino)fluorene-9-spiro-3'-(6'-dimethylamino)phthalide obtained in Example 16 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 49

Example 40 was repeated except that 3-diethylamino-6-(N-ethyl-N-tetrahydrofurfurylamino)fluorene-9-spiro-3'-(6'-dimethylamino)phthalide obtained in Example 17 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 50

Example 40 was repeated except that 3-di-n-butylamino-6-(N-methyl-N-tetrahydrofurfurylamino)fluorene-9-spiro-3'-(6'-dimethylamino)phthalide obtained in Example 18 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 51

Example 40 was repeated except that 3-pyrrolidino-6-(N-methyl-N-tetrahydrofurfurylamino)fluorene-9-spiro-3'-(6'-pyrrolidino)phthalide obtained in Example 19 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 52

Example 40 was repeated except that 3-dimethylamino-6-(N-ethyl-N-β-phenylethylamino)fluorene-9-spiro-3'-(6'-dimethylamino)phthalide obtained in Example 23 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 53

Example 40 was repeated except that 3-diethylamino-6-(N-methyl-N-α-phenylethylamino)fluorene-9-spiro-3'-(6'-dimethylamino)phthalide obtained in Example 24 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 54

Example 40 was repeated except that 3-diethylamino-6-(N-methyl-N-p-chlorobenzylamino)fluorene-9-spiro-3'-(6'-dimethylamino)phthalide obtained in Example 25 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 55

Example 40 was repeated except that 3-pyrrolidino-6-(N-ethyl-N-β-phenylethylamino)fluorene-9-spiro-3'-(6'-pyrrolidino)phthalide obtained in Example 26 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 56

Example 40 was repeated except that 3-dimethylamino-6-(N-methyl-N-phenoxyethylamino)fluorene-9-spiro-3'-(6'-dimethylamino)phthalide obtained in Example 30 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 57

Example 40 was repeated except that 3-diethylamino-6-(N-methyl-N-γ-chlorobenzylamino)fluorene-9-spiro-3'-(6'-dimethylamino)phthalide obtained in Example 31 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 58

Example 40 was repeated except that 3-di-n-butylamino-6-(N-ethyl-N-p-methoxyphenoxyethylamino)fluorene-9-spiro-3'-(6'-dimethylamino)phthalide obtained in Example 32 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 59

Example 40 was repeated except that 3-pyrrolidino-6-(N-methyl-N-p-chlorophenoxypropylamino)fluorene-9-spiro-3'-(6'-pyrrolidino)phthalide obtained in Example 33 was used instead of 3-dimethylamino-6-(N-ethyl-N-ethoxyethylamino)fluorene-9-spiro-3-(6'-dimethylamino)phthalide to obtain a heat-sensitive record material.

EXAMPLE 60

Example 40 was repeated except that 3-dimethylamino-6-(N-ethyl-N-2-chloroethylamino)fluorene-9-spiro-3'-(6'-dimethylamino)phthalide obtained in Example 35 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 61

Example 40 was repeated except that 3-diethylamino-6-(N-methyl-N-2-chloroethylamino)fluorene-9-spiro-3'-(6'-dimethylamino)phthalide obtained in Example 36 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 62

Example 40 was repeated except that 3-di-n-butylamino-6-(N-ethyl-N-3-chloro-n-propylamino)fluorene-9-spiro-3'-(6'-dimethylamino)phthalide obtained in Example 37 was used instead of 3-dimethylamino-6-(N-ethyl-N-ethoxyethylamino)fluorene-9-spiro-3'-(6'-dimethylamino)phthalide to obtain a heat-sensitive record material.

EXAMPLE 63

Example 40 was repeated except that 3-pyrrolidino-6-(N-methyl-N-2-bromoethylamino)fluorene-9-spiro-3'-(6'-pyrrolidino)phthalide obtained in Example 38 was used instead of 3-dimethylamino-6-(N-ethyl-N-ethoxyethylamino)fluorene-9-spiro-3'-(6'-dimethylamino)phthalide to obtain a heat-sensitive record material.

Controls 1 to 4

Example 40 was repeated except that the following phthalide derivatives were used instead of 3-dimethylamino-6-(N-ethyl-N-ethoxyethylamino)fluorene-9-spiro-3'-(6'-dimethylamino)phthalide to obtain four heat-sensitive record materials.

Control 1: 3,6-bis(dimethylamino)fluorene-9-spiro-3'-(6'-dimethylamino)phthalide (m.p. 245°~248° C.).

Control 2: 3-dimethylamino-6-dibenzylaminofluorene-9-spiro-3'-(6'-dimethylamino)phthalide (m.p. 238°~240° C.).

Control 3: 3-diethylamino-6-dimethylaminofluorene-9-spiro-3'-(6'-di-n-butylamino)phthalide (m.p. 179°~181° C.).

Control 4: 3-dimethylamino-6-piperidinofluorene-9-spiro-3'-(6'-dimethylamino)phthalide (m.p. 230°~232° C.).

The following properties of thus obtained heat-sensitive record materials were examined. The results are shown in Table 1.

(1) Fogging at near infrared region:

The optical density of the coated surface of each record materials before recording was measured at 850 nm with a spectrophotometer.

(2) Color developability at near infrared region:

Each record material was stayed on heated plate at 120° C. for 5 seconds with a pressure of 4 kg/cm² to develop a blue color image. The optical density (initial density) of the color image was measured in the same manner as in the above test 1.

(3) Moisture resistance at near infrared region:

The record materials after the above color decoloring test 2 were allowed to stand at 40° C. under 90% RH for 24 hours, and then the optical density of the developed color images was measured in the same manner as in the above test 1.

(4) Heat resistance at near infrared region:

The record materials after the above color developing test 2 were allowed to stand at 60° C. for 16 hours, and then the optical density of the developed color images was measured in the same manner as in the above test 1.

The discoloration degree (%), in the above tests 3 and 4, was calculated by the following equation.

$$\frac{\text{(initial density)} - \text{(density after treatment)}}{\text{(initial density)}} \times 100(\%)$$

TABLE 1

| | Fogging (Optical Density) | Color Developability (Initial Density) | Moisture Resistance | | Heat Resistance | |
|---|---|---|---|---|---|---|
| | | | Optical Density | Dis coloration Degree | Optical Density | Dis coloration Degree |
| Example 40 | 0.05 | 0.92 | 0.89 | 3.3 | 0.88 | 4.3 |
| Example 41 | 0.05 | 0.92 | 0.88 | 4.3 | 0.89 | 3.3 |
| Example 42 | 0.04 | 0.93 | 0.89 | 4.3 | 0.87 | 6.5 |
| Example 43 | 0.05 | 0.93 | 0.87 | 6.5 | 0.88 | 5.4 |
| Example 44 | 0.06 | 0.93 | 0.89 | 4.3 | 0.89 | 4.3 |
| Example 45 | 0.05 | 0.92 | 0.86 | 6.5 | 0.88 | 4.3 |
| Example 46 | 0.04 | 0.93 | 0.89 | 4.3 | 0.88 | 5.4 |
| Example 47 | 0.05 | 0.93 | 0.86 | 7.5 | 0.87 | 6.5 |
| Example 48 | 0.03 | 0.92 | 0.90 | 2.2 | 0.89 | 3.3 |
| Example 49 | 0.03 | 0.93 | 0.90 | 3.2 | 0.88 | 5.4 |
| Example 50 | 0.04 | 0.92 | 0.88 | 4.3 | 0.88 | 4.3 |
| Example 51 | 0.02 | 0.93 | 0.88 | 5.4 | 0.89 | 4.3 |
| Example 52 | 0.05 | 0.92 | 0.87 | 5.4 | 0.88 | 4.3 |
| Example 53 | 0.05 | 0.94 | 0.88 | 6.4 | 0.86 | 8.5 |
| Example 54 | 0.04 | 0.93 | 0.89 | 4.3 | 0.75 | 19.4 |
| Example 55 | 0.05 | 0.92 | 0.85 | 7.6 | 0.88 | 4.3 |
| Example 56 | 0.02 | 0.92 | 0.87 | 5.4 | 0.88 | 4.3 |
| Example 57 | 0.02 | 0.93 | 0.87 | 6.4 | 0.88 | 5.4 |
| Example 58 | 0.03 | 0.92 | 0.88 | 4.3 | 0.81 | 12.0 |
| Example 59 | 0.05 | 0.92 | 0.85 | 7.6 | 0.75 | 18.5 |
| Example 60 | 0.02 | 0.92 | 0.86 | 6.5 | 0.88 | 4.3 |
| Example 61 | 0.02 | 0.92 | 0.85 | 7.6 | 0.87 | 5.4 |
| Example 62 | 0.03 | 0.93 | 0.88 | 5.3 | 0.82 | 11.8 |
| Example 63 | 0.04 | 0.92 | 0.86 | 6.5 | 0.76 | 17.3 |
| Control 1 | 0.06 | 0.92 | 0.56 | 39.1 | 0.50 | 45.7 |
| Control 2 | 0.06 | 0.80 | 0.30 | 62.5 | 0.24 | 70.0 |
| Control 3 | 0.05 | 0.92 | 0.57 | 38.0 | 0.48 | 47.8 |
| Control 4 | 0.05 | 0.79 | 0.25 | 68.3 | 0.23 | 70.9 |

EXAMPLE 64

A pressure-sensitive record material was prepared by the following method with the use of 3-dimethylamino-6-(N-ethyl-N-ethoxyethylamino)fluorene-9-spiro-3'-(6'-dimethylamino)phthalide obtained in Example 1.

3 parts of the above phthalide derivative was dissolved in 100 parts of isopropylated naphthalene. The resultant solution was dispersed in 350 parts of warm water (50° C.) containing 25 parts of pigskin-gelatin having an isoelectric point of 8 and 25 parts of gum arabic dissolved on it to obtain an emulsion. 1000 parts of warm water was added to the emulsion. The mixture was adjusted to pH 4 with acetic acid and cooled at 10° C. 10 parts of 25% aqueous solution of glutaraldehyde was added to it to solidify capsules. The capsule-containing coating composition was coated on one surface of a base sheet of 45 g/m$^2$ in the weight of 5 g/m$^2$ on dry basis and an acceptor coating composition comprising 20 parts of zinc 3,5-bis(α-methylbenzyl)salicylate, 80 parts of kaolin and 30 parts of styrene-butadiene copolymer emulsion (solid content: 50%) dispersed in 200 parts of water was coated on another surface of the base sheet in the weight of 5 g/m$^2$ on dry basis to obtain a pressure-sensitive record material (middle sheet).

Several of the pressure-sensitive record material were piled in the manner as the capsule coated layer was closed to the acceptor coated layer, pressed with driving a pen to obtain blue images on the acceptor coated surface. The color images were stable under the circumstances of high temperature and high humidity. Further, when the color images were exposed to sunlight, the color change and discolouration were not appreciated. The light absorption spectrum had a broad strong absorption of 590~900 nm.

EXAMPLE 65

Example 64 was repeated except that 3-diethylamino-6-(N-methyl-N-allylamino)fluorene-9-spiro-3'-(6'-dimethylamino)phthalide obtained in Example 9 was used instead of 3-dimethylamino-6-(N-ethyl-N-ethoxyethylamino)fluorene-9-spiro-3'-(6'-dimethylamino)phthalide to obtain a pressure-sensitive record material.

The color images developed in the same manner as in Example 64 were stable under the circumstances of high temperature and high humidity. When exposed to sunlight, the color change and discolouration were not appreciated. The light absorption spectrum had a broad strong absorption at 590~900 nm.

EXAMPLE 66

Example 64 was repeated except that 3-dimethylamino-6-(N-methyl-N-tetrahydrofurfurylamino)- fluorene-9-spiro-3'-(6'-dimethylamino)phthalide obtained in Example 16 was used instead of 3-dimethylamino-6-(N-ethyl-N-ethoxyethylamino)fluorene-9-spiro-3'-(6'-dimethylamino)phthalide to obtain a pressure-sensitive record material.

The color images developed in the same manner as in Example 64 were stable under the circumstances of high temperature and high humidity. When exposed to sunlight, the color change and discolouration were not appreciated. The light absorption spectrum had a broad strong absorption at 590~900 nm.

EXAMPLE 67

Example 64 was repeated except that 3-dimethylamino-6-(N-ethyl-N-β-phenylethylamino)fluorene-9-spiro-3'-(6'-dimethylamino)phthalide obtained in Example 23 was used instead of 3-dimethylamino-6-(N-ethyl-N-ethoxyethylamino)fluorene-9-spiro-3'-(6'-dimethylamino)phthalide to obtain a pressure-sensitive record material.

The color images developed in the same manner as in Example 64 were stable under the circumstances of high temperature and high humidity. When exposed to sunlight, the color change and discolouration were not appreciated. The light absorption spectrum had a broad strong absorption at 590~900 nm.

EXAMPLE 68

Example 64 was repeated except that 3-dimethylamino-6-(N-methyl-N-phenoxyethylamino)fluorene-9-spiro-3'-(6'-dimethylamino)phthalide obtained in Example 30 was used instead of 3-dimethylamino-6-(N-ethyl-N-ethoxyethylamino)fluorene-9-spiro-3'-(6'-dimethylamino)phthalide to obtain a pressure-sensitive record material.

The color images developed in the same manner as in Example 64 were stable under the circumstances of high temperature and high humidity. When exposed to sunlight, the color change and discolouration were not appreciated. The light absorption spectrum had a broad strong absorption at 590~900 nm.

EXAMPLE 69

Example 64 was repeated except that 3-dimethylamino-6-(N-ethyl-N-2-chloroethylamino)fluorene-9-spiro-3'-(6'-dimethylamino)phthalide obtained in Example 35 was used instead of 3-dimethylamino-6-(N-ethyl-N-ethoxyethylamino)fluorene-9-spiro-3'-(6'-dimethylamino)phthalide to obtain a pressure-sensitive record material.

The color images developed in the same manner as in Example 64 were stable under the circumstances of high temperature and high humidity. When exposed to sunlight, the color change and discolouration were not appreciated. The light absorption spectrum had a broad strong absorption at 590~900 nm.

EXAMPLE 70

An electrothermal record material was prepared by the following method with the use of the phthalide derivaitve obtained in Example 4.

200 parts of cuprous iodide and 5 parts of 10% aqueous solution of sodium sulfite were added to 200 parts of 1% aqueous solution of polyvinyl alcohol. The mixtur was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m² in the weight of 7 g/m² on dry basis. Further, there was coated on the coating layer in the weight of 5 g/m² on dry basis a heat-sensitive coating composition prepared in Example 43 with the use of 3-pyrrolidino-6-(N-ethyl-N-ethoxyethylamino)fluorene-9-spiro-3'-(6'-pyrrolidino)phthalide obtained in Example 4 to obtain an electrothermal record material.

Images were recorded on the record material with the use of a cylindrical scanning recording machine at a scanning speed of 630 mm/sec with a needle pressure of 10 g. The recorded images were deep blue and superior in heat resistance and moisture resistance. The light absorption spectrum of them had a strong absorption at 480 nm and a broad strong absorption at 600~900 nm.

EXAMPLE 71

An electrothermal record material was prepared in the same manner as in Example 70 except that the phthalide derivaitve obtained in Example 12 was used instead of 3-pyrrolidino-6-(N-ethyl-N-ethoxyethylamino)fluorene-9-spiro-3'-(6'-pyrrolidino)phthalide.

The recorded images produced in the same manner as in Example 70 were deep blue and superior in heat resistance and moisture resistance. The light absorption spectrum of them had a strong absorption at 480 nm and a broad strong absorption at 600~900 nm.

EXAMPLE 72

An electrothermal record material was prepared in the same manner as in Example 70 except that the phthalide derivaitve obtained in Example 19 was used instead of 3-pyrrolidino-6-(N-ethyl-N-ethoxyethylamino)fluorene-9-spiro-3'-(6'-pyrrolidino)phthalide.

The recorded images produced in the same manner as in Example 70 were deep blue and superior in heat resistance and moisture resistance. The light absorption spectrum of them had a strong absorption at 480 nm and a broad strong absorption at 600~900 nm.

EXAMPLE 73

An electrothermal record material was prepared in the same manner as in Example 70 except that the phthalide derivaitve obtained in Example 26 was used instead of 3-pyrrolidino-6-(N-ethyl-N-ethoxyethylamino)fluorene-9-spiro-3'-(6'-pyrrolidino)phthalide.

The recorded images produced in the same manner as in Example 70 were deep blue and superior in heat resistance and moisture resistance. The light absorption spectrum of them had a strong absorption at 480 nm and a broad strong absorption at 600~900 nm.

EXAMPLE 74

An electrothermal record material was prepared in the same manner as in Example 70 except that the phthalide derivaitve obtained in Example 33 was used instead of 3-pyrrolidino-6-(N-ethyl-N-ethoxyethylamino)fluorene-9-spiro-3'-(6'-pyrrolidino)phthalide.

The recorded images produced in the same manner as in Example 70 were deep blue and superior in heat resistance and moisture resistance. The light absorption spectrum of them had a strong absorption at 480 nm and a broad strong absorption at 600~900 nm.

EXAMPLE 75

An electrothermal record material was prepared in the same manner as in Example 70 except that the phthalide derivaitve obtained in Example 38 was used instead of 3-pyrrolidino-6-(N-ethyl-N-ethoxyethylamino)fluorene-9-spiro-3'-(6'-pyrrolidino)phthalide.

The recorded images produced in the same manner as in Example 70 were deep blue and superior in heat resistance and moisture resistance. The light absorption spectrum of them had a strong absorption at 480 nm and a broad strong absorption at 600~900 nm.

EXAMPLE 76

A photosensitive record material was prepared by the following method with the use of the phthalide derivative obtained in Example 5.

6 g of 3-(N-methyl-N-cyclohexylamino)-6-(N-ethyl-N-ethoxyethylamino)fluorene-9-spiro-3'-(6'-dimethylamino)phthalide were dissolved in 40 ml of chloroform. 40 ml of 10% benzene solution of polystyrene and 5 g of carbon tetrabromide were added to the solution and the mixture was thoroughly stirred to prepare a coating composition, the coating composition was coated on polyethylene laminated paper having polyethylene at the both surfaces in the weight of 5 g/m² on dry basis in a dark place. The coated paper was irradiated with a light of eight ultraviolet lamps of 20 W from a distance of 5 cm for 10 minutes to develop green color images. The color images were then fixed by rinsing with a solution of acetone/n-hexane (1/5).

The resultant images were stable under the circumstances of high temperature and high humidity. The light absorption spectrum had a strong absorption at 480 nm and a broad strong absorption at 630~900 nm.

EXAMPLE 77

A photosensitive record material was prepared in the same manner as in Example 76 except that 3-(N-methyl-N-cyclohexylamino)-6-(N-ethyl-N-propargylamino)-fluorene-9-spiro-3'-(6'-dimethylamino)phthalide obtained in Example 13 was used instead of 3-(N-methyl-N-cyclohexylamino)-6-(N-ethyl-N-ethoxyethylamino)-fluorene-9-spiro-3'-(6'-dimethylamino)phthalide.

The blue images developed on the record material in the same manner as in Example 76 were stable under the circumstances of high temperature and high humidity. The light absorption spectrum had a strong absorption at 480 nm and a broad strong absorption at 630~900 nm.

EXAMPLE 78

A photosensitive record material was prepared in the same manner as in Example 76 except that 3-(N-methyl-N-cyclohexylamino)-6-(N-ethyl-N-tetrahydropyran-2-methylamino)fluorene-9-spiro-3'-(6'-dimethylamino)phthalide obtained in Example 20 was used instead of 3-(N-methyl-N-cyclohexylamino)-6-(N-ethyl-N-ethoxyethylamino)fluorene-9-spiro-3'-(6'-dimethylamino)phthalide.

The blue images developed on the record material in the same manner as in Example 76 were stable under the circumstances of high temperature and high humidity. The light absorption spectrum had a strong absorption at 480 nm and a broad strong absorption at 630~900 nm.

EXAMPLE 79

A photosensitive record material was prepared in the same manner as in Example 76 except that 3-(di-n-butylamino)-6-(N-methyl-N-α-phenylethylamino)fluorene-9-spiro-3'-(6'-dimethylamino)phthalide obtained in Example 27 was used instead of 3-(N-methyl-N-cyclohexylamino)-6-(N-ethyl-N-ethoxyethylamino)-fluorene-9-spiro-3'-(6'-dimethylamino)phthalide.

The blue images developed on the record material in the same manner as in Example 76 were stable under the circumstances of high temperature and high humidity. The light absorption spectrum had a strong absorption at 480 nm and a broad strong absorption at 630~900 nm.

EXAMPLE 80

A photosensitive record material was prepared in the same manner as in Example 76 except that 3-(N-methyl-N-cyclohexylamino)-6-(N-methyl-N-p-methylphenoxyethylamino)fluorene-9-spiro-3'-(6'-dimethylamino)phthalide obtained in Example 34 was used instead of 3-(N-methyl-N-cyclohexylamino)-6-(N-ethyl-N-ethoxyethylamino)fluorene-9-spiro-3'-(6'-dimethylamino)phthalide.

The blue images developed on the record material in the same manner as in Example 76 were stable under the circumstances of high temperature and high humidity. The light absorption spectrum had a strong absorption at 475 nm and a broad strong absorption at 630~900 nm.

EXAMPLE 81

A photosensitive record material was prepared in the same manner as in Example 76 except that 3-(N-methyl-N-cyclohexylamino)-6-(N-methyl-N-4-bromo-n-butylamino)fluorene-9-spiro-3'-(6'-dimethylamino)phthalide obtained in Example 39 was used instead of 3-(N-methyl-N-cyclohexylamino)-6-(N-ethyl-N-ethoxyethylamino)fluorene-9-spiro-3'-(6'-dimethylamino)phthalide.

The blue images developed on the record material in the same manner as in Example 76 were stable under the circumstances of high temperature and high humidity. The light absorption spectrum had a strong absorption at 473 nm and a broad strong absorption at 630~900 nm.

EXAMPLE 82

An ultrasonic vibrator of needle type having a radius of 0.2 mm was slightly contacted on a surface of the heat-sensitive record material obtained in Example 40 and the record material was moved at a speed of 20 cm/sec under an ultrasonic vibration of 19 KHz 20 W to obtain blue recorded images superior in heat resistance and moisture resistance.

EXAMPLE 83

An ultrasonic vibrator of needle type having a radius of 0.2 mm was slightly contacted on a surface of the heat-sensitive record material obtained in Example 44 and the record material was moved at a speed of 20 cm/sec under an ultrasonic vibration of 19 KHz 20 W to obtain blue recorded images superior in heat resistance and moisture resistance.

EXAMPLE 84

An ultrasonic vibrator of needle type having a radius of 0.2 mm was slightly contacted on a surface of the heat-sensitive record material obtained in Example 48 and the record material was moved at a speed of 20 cm/sec under an ultrasonic vibration of 19 KHz 20 W to obtain blue recorded images superior in heat resistance and moisture resistance.

EXAMPLE 85

An ultrasonic vibrator of needle type having a radius of 0.2 mm was slightly contacted on a surface of the heat-sensitive record material obtained in Example 52 and the record material was moved at a speed of 20 cm/sec under an ultrasonic vibration of 19 KHz 20 W to obtain blue recorded images superior in heat resistance and moisture resistance.

EXAMPLE 86

An ultrasonic vibrator of needle type having a radius of 0.2 mm was slightly contacted on a surface of the heat-sensitive record material obtained in Example 56 and the record material was moved at a speed of 20 cm/sec under an ultrasonic vibration of 19 KHz 20 W to obtain blue recorded images superior in heat resistance and moisture resistance.

EXAMPLE 87

An ultrasonic vibrator of needle type having a radius of 0.2 mm was slightly contacted on a surface of the heat-sensitive record material obtained in Example 60 and the record material was moved at a speed of 20 cm/sec under an ultrasonic vibration of 19 KHz 20 W to obtain blue recorded images superior in heat resistance and moisture resistance.

What we claim is:

1. A recording system which utilizes the color forming reaction between a colorless chromogenic material and an electron accepting acid reactant material, comprising a base sheet and a chromogenic material which comprises at least one phthalide derivative having the following formula:

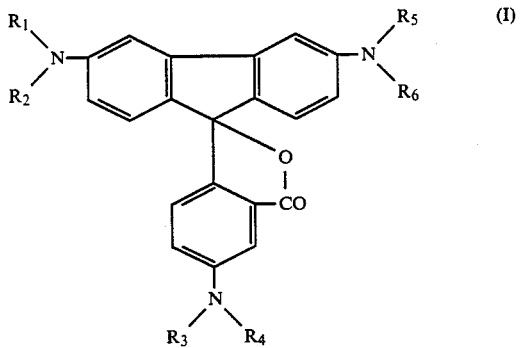

wherein at least one of $R_1$, $R_2$, $R_3$, $R_4$, $R_5$ and $R_6$ radicals is an alkoxyalkyl having 3 to 8 carbon atoms; an unsaturated alkyl having 3 to 9 carbon atoms, tetrahydrofurfuryl; tetrahydropyran-2-methyl; an aralkyl represented by the following formula

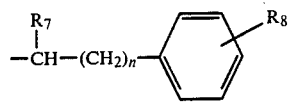

in which n is 0, 1 or 2, $R_7$ is hydrogen or an alkyl having 1 to 4 carbon atoms and $R_8$ is hydrogen, halogen, an alkyl having 1 to 4 carbon atoms or an alkoxyl having 1 to 4 carbon atoms, and when n is 0 and $R_7$ is hydrogen, $R_8$ is halogen or an alkoxy having 1 to 4 carbon atoms; an alkyl having 2 to 8 carbon atoms and having phenoxy group which may be substituted by at least one selected from the group consisting of halogens, alkyls having 1 to 4 carbon atoms, and alkoxyls having 1 to 4 carbon atoms; or a halogenated alkyl having 1 to 8 carbon atoms; and each of the other ones of said radicals is hydrogen; an alkyl having 1 to 8 carbon atoms which may be substituted by at least one halogen; a cycloalkyl having 5 to 12 carbon atoms; an alkoxyalkyl having 3 to 8 carbon atoms; an unsaturated alkyl having 3 to 9 carbon atoms; tetrahydrofurfuryl; tetrahydropyran-2-methyl; an aralkyl which may be substituted by at least one selected from the group consisting of halogens, alkyls having 1 to 4 carbon atoms and alkoxyls having 1 to 4 carbon atoms; an aryl which may be substituted by at least one selected from the group consisting of halogens, alkyls having 1 to 4 carbon atoms and alkoxys having 1 to 4 carbon atoms; or an alkyl having 2 to 8 carbon atoms and having phenoxy group which may be substituted by at least one selected from the group consisting of halogens, alkyls having 1 to 4 carbon atoms, and alkoxyls having 1 to 4 carbon atoms; or one or two pairs of $R_1$ and $R_2$, $R_3$ and $R_4$, and $R_5$ and $R_6$ may form morpholino, pyrrolidino, piperidino or hexamethyleneimino group together with the adjacent nitrogen atom.

2. A recording system as defined in claim 1, wherein said recording system is a pressure-sensitive recording system.

3. A recording system as defined in claim 1, wherein said recording system is a heat-sensitive recording system.

* * * * *